(12) United States Patent
Ohtake et al.

(10) Patent No.: US 10,646,317 B2
(45) Date of Patent: May 12, 2020

(54) OCCLUSAL STATE IDENTIFYING METHOD, OCCLUSAL STATE IDENTIFYING APPARATUS, AND STORAGE MEDIUM

(71) Applicant: FUJITSU LIMITED, Kawasaki-shi, Kanagawa (JP)

(72) Inventors: Ryosuke Ohtake, Atsugi (JP); Katsumi Umekawa, Yokohama (JP); Tatsukiyo Ishimura, Kawasaki (JP)

(73) Assignee: FUJITSU LIMITED, Kawasaki (JP)

( * ) Notice: Subject to any disclaimer, the term of this patent is extended or adjusted under 35 U.S.C. 154(b) by 282 days.

(21) Appl. No.: 15/861,125

(22) Filed: Jan. 3, 2018

(65) Prior Publication Data

US 2018/0206958 A1 Jul. 26, 2018

(30) Foreign Application Priority Data

Jan. 25, 2017 (JP) .................................. 2017-011106

(51) Int. Cl.
*A61C 19/05* (2006.01)
*G06T 19/20* (2011.01)
(Continued)

(52) U.S. Cl.
CPC .............. *A61C 19/05* (2013.01); *G06T 19/20* (2013.01); *A61C 2007/004* (2013.01); *G16H 50/50* (2018.01)

(58) Field of Classification Search
CPC ... A61C 19/05; A61C 2007/004; G06T 19/20; G16H 50/50
See application file for complete search history.

(56) References Cited

U.S. PATENT DOCUMENTS

| 5,905,658 A | 5/1999 | Baba |
| 2006/0072810 A1 | 4/2006 | Scharlack et al. |

(Continued)

FOREIGN PATENT DOCUMENTS

| JP | 08-168937 | 7/1996 |
| JP | 09-238963 | 9/1997 |

(Continued)

OTHER PUBLICATIONS

Machine translation of Myriam et al (JP 2013537076), accessed Dec. 5, 2019, Google patents, pp. 1-11 (Year: 2019).*

(Continued)

*Primary Examiner* — Edward Park
(74) *Attorney, Agent, or Firm* — Fujitsu Patent Center

(57) ABSTRACT

An occlusal state identifying method executed by a processor included in an occlusal state identifying apparatus, the occlusal state identifying method includes obtaining maxillary shape data and mandibular shape data; arranging a maxillary image including a plurality of maxillary teeth corresponding to the obtained maxillary shape data and a mandibular image including a plurality of mandibular teeth corresponding to the obtained mandibular shape data such that corresponding teeth oppose each other; executing a moving process of moving at least one of the arranged maxillary image and mandibular image by executing a dynamic simulation; and identifying a positional relationship between the maxillary image and the mandibular image after the moving process as a positional relationship corresponding to an occlusal state of the maxillary teeth included in the maxillary image and the mandibular teeth included in the mandibular image.

15 Claims, 18 Drawing Sheets

(51) Int. Cl.
*G16H 50/50* (2018.01)
*A61C 7/00* (2006.01)

(56) References Cited

U.S. PATENT DOCUMENTS

| | | |
|---|---|---|
| 2012/0072177 A1 | 3/2012 | Manai et al. |
| 2013/0066598 A1 | 3/2013 | Fisker et al. |
| 2013/0275107 A1 | 10/2013 | Alpern et al. |

FOREIGN PATENT DOCUMENTS

| | | | |
|---|---|---|---|
| JP | 2009-501616 | | 1/2009 |
| JP | 2012-45247 | | 3/2012 |
| JP | 2013-520251 | | 6/2013 |
| JP | 2013-537076 A | | 9/2013 |
| JP | 2013537076 | * | 9/2013 |
| KR | 10-2013-0048202 A | | 5/2013 |
| KR | 20130048202 | * | 5/2013 |
| WO | 2011/103876 A1 | | 9/2011 |

OTHER PUBLICATIONS

Machine translation of Kabell et al (KR 20130048202), accessed Dec. 5, 2019, Google patents, pp. 1-23 (Year: 2019).*
Extended European Search Report dated May 22, 2018 for corresponding European Patent Application No. 18150724.5, 7 pages.
Korean Office Action dated Nov. 29, 2018 for corresponding Korean Patent Application No. 10-2018-0007755, with English Translation, 13 pages.

* cited by examiner

FIG. 15
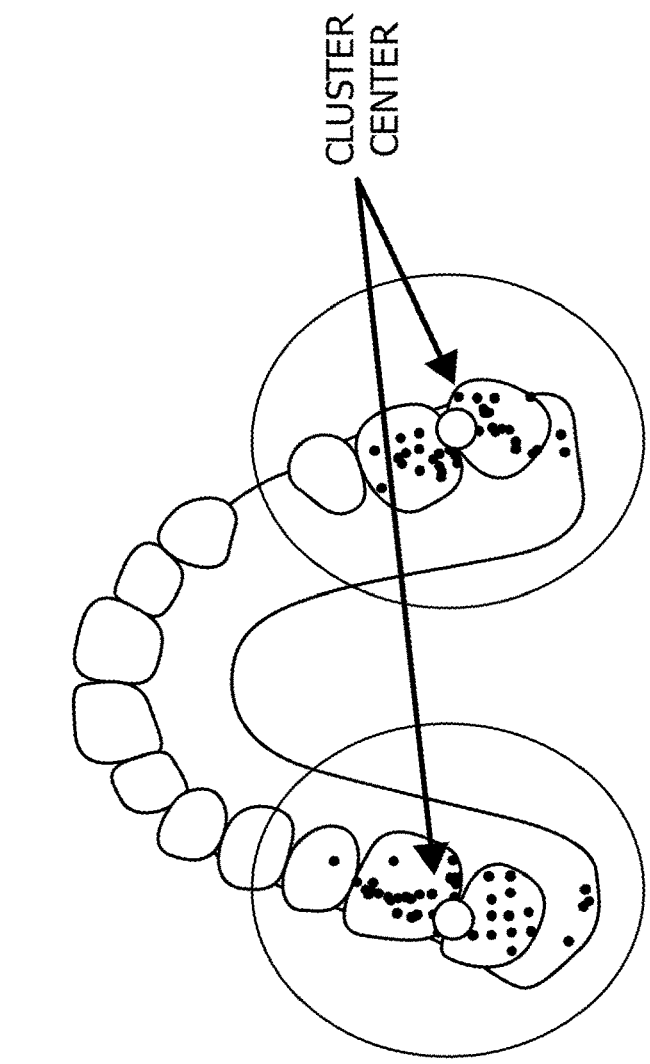
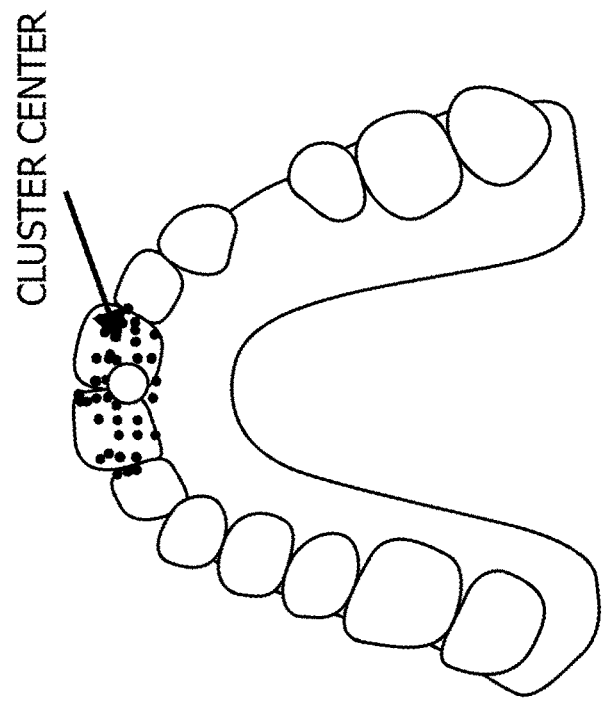

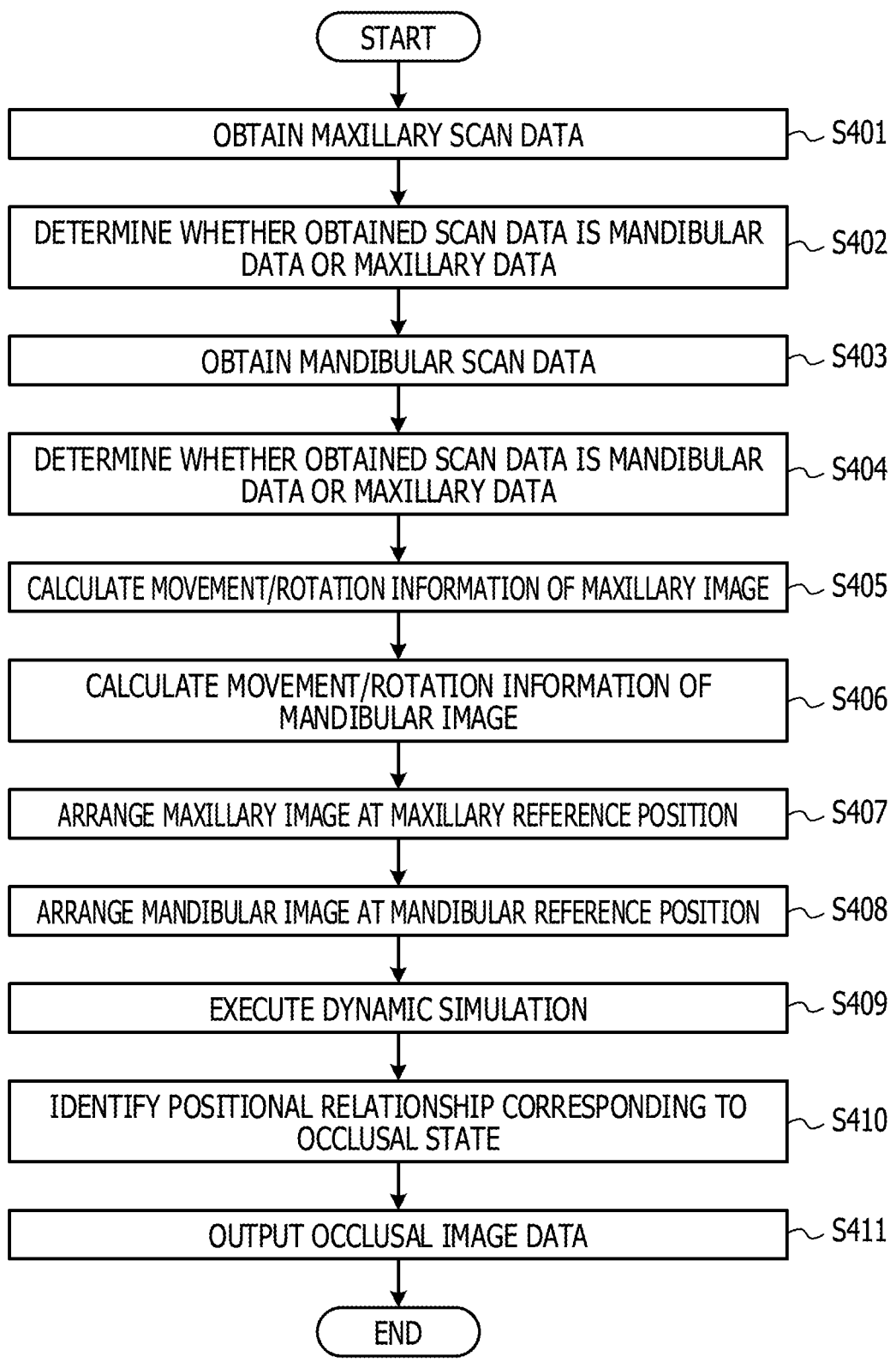

OCCLUSAL STATE IDENTIFYING METHOD, OCCLUSAL STATE IDENTIFYING APPARATUS, AND STORAGE MEDIUM

CROSS-REFERENCE TO RELATED APPLICATION

This application is based upon and claims the benefit of priority of the prior Japanese Patent Application No. 2017-11106, filed on Jan. 25, 2017, the entire contents of which are incorporated herein by reference.

FIELD

The embodiment discussed herein is related to an occlusal state identifying method, an occlusal state identifying apparatus, and a storage medium.

BACKGROUND

It is known that tooth-form data indicating tooth forms including the shapes of crowns of teeth is used in dental computer-aided design (CAD) and computer-aided manufacturing (CAM) software with various functions. For example, it is known that arrangement information indicating the positional relationship between at least a subject's first molar and second molar is obtained from a captured image of the subject's oral cavity, and, from the obtained arrangement information, the eruption date of another subject's second molar is predicted (for example, see Japanese Laid-open Patent Publication No. 2012-45247). It is also known that the position and direction of an object for recognition are detected, and, by using the object for recognition whose position and direction are detected, the spatial relationship between a dental patient's maxilla and mandible is captured (for example, see Japanese National Publication of International Patent Application No. 2009-501616).

It is known that the coordinates of movement measurement data at the maximal intercuspal position obtained from the masticatory movement locus of a dentition are matched to the coordinates of shape data obtained from a dentition plaster model of the maxilla and the mandible in a basic state by a conversion matrix (for example, see Japanese Laid-open Patent Publication No. 9-238963). It is known that a collision between 3D models is calculated using a boundary volume layer such as an AABB tree and a spatial distribution structure such as a BSP tree, Oct-tree, and kd tree, and an occlusal position where a virtual maxilla and a virtual mandible contact each other is detected (for example, see Japanese National Publication of International Patent Application No. 2013-520251).

However, a jaw image corresponding to scan data obtained by a dental 3D scanner device has a direction and a tilt in accordance with a scan state. The direction and position of the jaw image is modified by a user who uses the jaw image to a desired direction and position. For example, to use a virtual articulator that simulates a human jaw movement in order to create a dental prosthesis, a user may arrange a maxillary image and a mandibular image such that an occlusal surface passing through a portion where maxillary teeth occlude with mandibular teeth matches a certain reference surface. It is burdensome to arrange the maxillary image and the mandibular image on a CAD screen such that the occlusal surface matches the certain reference surface. The process of arranging the maxillary image and the mandibular image such that the occlusal surface matches the certain reference surface may place an excessive burden on the user.

An occlusal image in a state where maxillary teeth occlude with mandibular teeth is obtained by superimposing maxillary and mandibular scan data obtained by separately scanning the maxillary teeth and the mandibular teeth on fitting scan data obtained by scanning the maxillary teeth and the mandibular teeth in an occlusal state. To omit the process of obtaining fitting scan data, various technologies are proposed to generate an occlusal image by combining a maxillary image corresponding to maxillary scan data and a mandibular image corresponding to a mandibular scan data. However, a maxillary image and a mandibular image each have a direction and a tilt in accordance with a scan state. Therefore, it is not easy to adjust the positional relationship between a maxillary image and a mandibular image, each having a direction and a tilt in accordance with a scan state, to be able to generate an occlusal image. In view of the above circumstances, it is desirable to identify the occlusal state of a maxillary image and a mandibular image corresponding respectively to maxillary teeth shape data and mandibular teeth shape data.

SUMMARY

According to an aspect of the invention, an occlusal state identifying method executed by a processor included in an occlusal state identifying apparatus, the occlusal state identifying method includes obtaining maxillary shape data and mandibular shape data; arranging a maxillary image including a plurality of maxillary teeth corresponding to the obtained maxillary shape data and a mandibular image including a plurality of mandibular teeth corresponding to the obtained mandibular shape data such that corresponding teeth oppose each other; executing a moving process of moving at least one of the arranged maxillary image and mandibular image by executing a dynamic simulation; and identifying a positional relationship between the maxillary image and the mandibular image after the moving process as a positional relationship corresponding to an occlusal state of the maxillary teeth included in the maxillary image and the mandibular teeth included in the mandibular image.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

BRIEF DESCRIPTION OF DRAWINGS

FIG. 15 is a diagram for describing an example that uses the left and right mandibular first teeth, mandibular sixth teeth, and mandibular seventh teeth in the case of executing the movement/rotation information generating process;

FIG. 18 is a flowchart of an occlusal state identifying process performed by the occlusal state identifying apparatus illustrated in FIG. 17.

DESCRIPTION OF EMBODIMENT

Hereinafter, an occlusal state identifying method, an occlusal state identifying apparatus, and a storage medium will be described with reference to the drawings. It is intended that the technical scope of the present application be not limited to an embodiment of the present application, and equivalents to the scope of the claims be included within the scope of the present application.

Figure 1B:
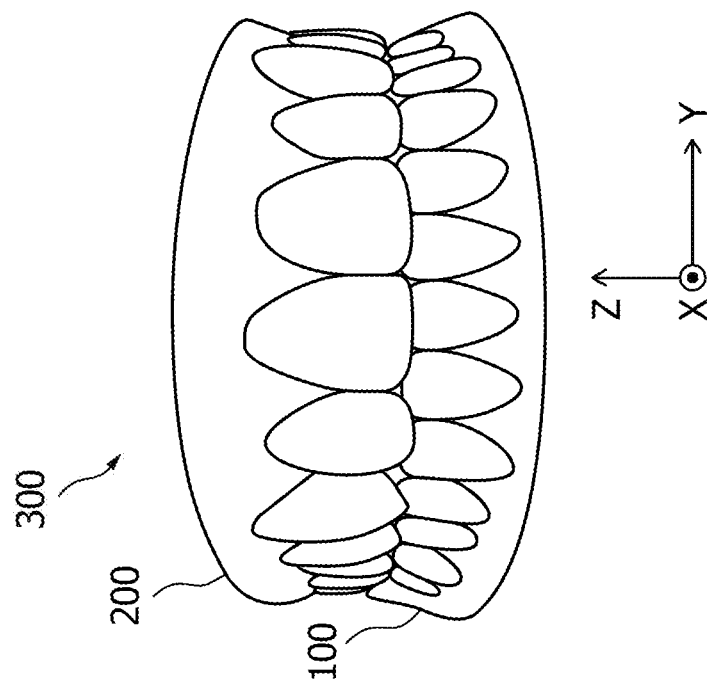
FIG. 1B is a diagram illustrating an example of an occlusal image where the maxillary image illustrated in FIG. 1A is moved by executing a dynamic simulation to bring maxillary teeth and mandibular teeth into occlusion.
Figure 1A:
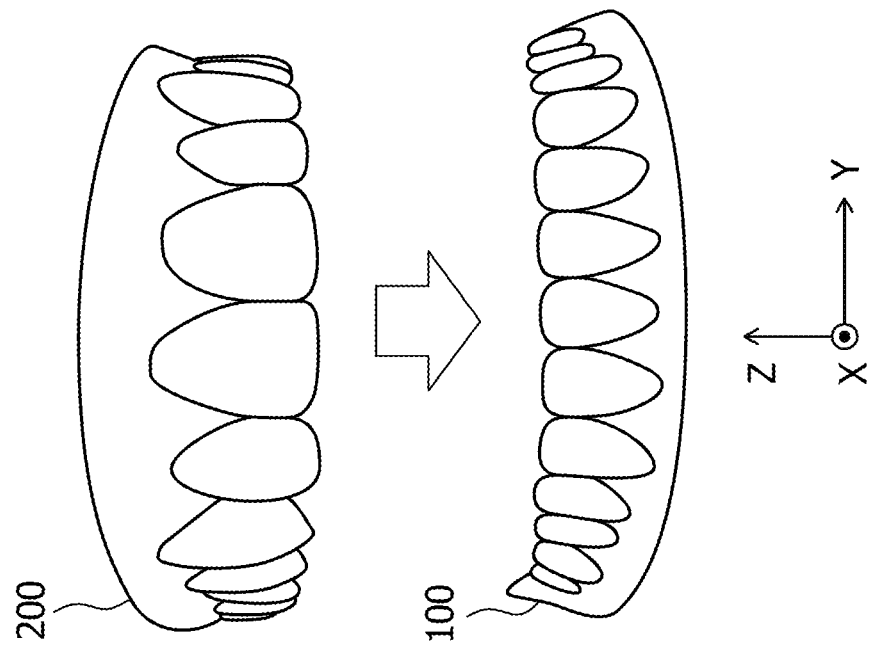
FIG. 1A is a diagram illustrating an example of oppositely-arranged images where a maxillary image and a mandibular image are arranged such that corresponding teeth oppose each other.

FIG. 1A is a diagram illustrating an example of oppositely-arranged images where a maxillary image and a mandibular image are arranged such that corresponding teeth oppose each other. FIG. 1B is a diagram illustrating an example of an occlusal image where the maxillary image illustrated in FIG. 1A is moved by executing a dynamic simulation to bring maxillary teeth and mandibular teeth into occlusion.

In an occlusal state identifying computer program, a jaw shape data obtaining unit obtains mandibular shape data indicating a mandibular image 100 and maxillary shape data indicating a maxillary image 200. In one example, mandibular shape data and maxillary shape data are items of scan data obtained by a dental 3D scanner device.

Next, a jaw image arranging unit arranges the maxillary image 200 and the mandibular image 100 such that corresponding teeth oppose each other. In one example, the jaw image arranging unit arranges the mandibular image 100 and the maxillary image 200 such that the X coordinate and the Y coordinate of the center of gravity of the left and right mandibular first teeth of the mandibular image 100 and the maxillary image 200 match each other. The jaw image arranging unit arranges the mandibular image 100 and the maxillary image 200 such that the X coordinate and the Y coordinate of the center of gravity of the left mandibular sixth tooth of the mandibular image 100 and the maxillary image 200 match each other. Furthermore, the jaw image arranging unit arranges the mandibular image 100 and the maxillary image 200 such that the X coordinate and the Y coordinate of the center of gravity of the right mandibular sixth tooth of the mandibular image 100 and the maxillary image 200 match each other.

Next, a dynamic simulation executing unit executes a moving process of moving at least one of the maxillary image 200 and the mandibular image 100, which are arranged such that the corresponding teeth oppose each other, by executing a dynamic simulation. In one example, the dynamic simulation executing unit defines the maxilla included in the maxillary image 200 as a substance having a uniform mass per unit surface area. The dynamic simulation executing unit executes a dynamic simulation to cause the maxilla included in the maxillary image 200 to fall naturally in the −Z direction. The dynamic simulation executing unit defines a state where maxillary teeth included in the maxillary image 200, which has fallen naturally as a result of the dynamic simulation, collide with mandibular teeth included in the mandibular image 100 and stop as a positional relationship indicating an occlusal state.

Next, a positional relationship identifying unit identifies the positional relationship between the maxillary image 200 and the mandibular image 100 after the moving process as a positional relationship corresponding to an occlusal state of the maxillary teeth included in the maxillary image 200 and the mandibular teeth included in the mandibular image 100. The positional relationship identifying unit defines a state where the maxillary teeth included in the maxillary image 200, which has fallen naturally, collide with the mandibular teeth included in the mandibular image 100 and stop as a positional relationship indicating an occlusal state.

An occlusal image output unit outputs occlusal image data indicating an occlusal image 300 including the maxillary image 200 and the mandibular image 100 identified as having a positional relationship corresponding to an occlusal state.

The occlusal state identifying program according to the embodiment may generate a fitting image indicating an occlusal state without using scan data indicating an occlusal state, by moving at least one of a maxillary image and a mandibular image through execution of a dynamic simulation.

Figure 2:
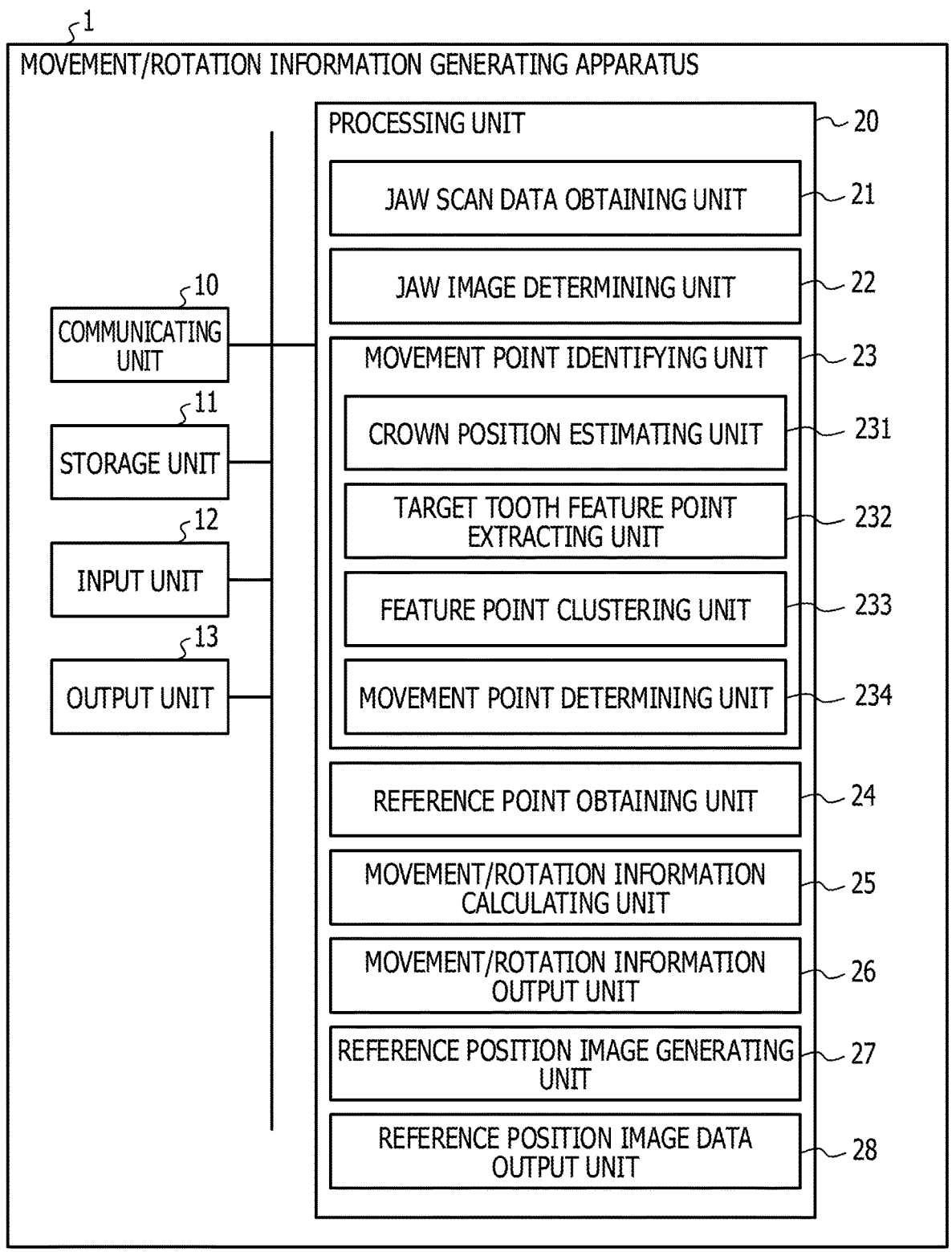
FIG. 2 is a block diagram of a movement/rotation information generating apparatus according to an embodiment.

FIG. 2 is a block diagram of a movement/rotation information generating apparatus according to the embodiment.

A movement/rotation information generating apparatus 1 includes a communicating unit 10, a storage unit 11, an input unit 12, an output unit 13, and a processing unit 20.

The communicating unit 10 communicates with a server or the like (not illustrated) via the Internet in accordance with the Hypertext Transfer Protocol (HTTP). The communicating unit 10 supplies data received from the server or the like to the processing unit 20. The communicating unit 10 transmits data supplied from the processing unit 20 to the server or the like.

The storage unit 11 includes at least one of, for example, a semiconductor device, a magnetic tape unit, a magnetic disk drive, and an optical disk drive. The storage unit 11 stores an operating system program, driver programs, application programs, data, and the like used in processing performed by the processing unit 20. For example, the storage unit 11 stores, as an application program, a movement/rotation information calculating computer program for causing the processing unit 20 to execute a movement/rotation information calculating process of calculating movement/rotation information indicating a movement amount and a rotation amount of a movement surface indicating the position of teeth. The storage unit 11 stores, as an application program, an occlusal state identifying computer program for causing the processing unit 20 to execute a positional relationship identifying process of identifying the positional relationship between a maxillary image and a mandibular image after a moving process as a positional relationship corresponding to an occlusal state of maxillary teeth included in the maxillary image and mandibular teeth included in the mandibular image. The movement/rotation information calculating program and the occlusal state identifying program may be installed in the storage unit 11 using a known set-up program or the like from a computer-readable portable recording medium such as compact-disc read-only memory (CD-ROM) and digital versatile disc (DVD)-ROM The storage unit 11 stores, as data, data and the like used in input processing. Furthermore, the storage unit 11 may temporarily store data that is temporarily used in processing such as input processing.

The input unit 12 may be any device as long as it can input data. The input unit 12 is, for example, a touchscreen or a key button. Using the input unit 12, an operator may enter characters, numerals, symbols, and the like. When operated by an operator, the input unit 12 generates a signal corresponding to that operation. The generated signal is supplied as the operator's instruction to the processing unit 20.

The output unit 13 may be any device as long as it can display video images, frames, and the like. The output unit 13 is, for example, a liquid crystal display (LCD) or an organic electro-luminescence (EL) display. The output unit 13 displays a video image in accordance with video data or a frame in accordance with moving image data supplied from the processing unit 20. The output unit 13 may be an output device that prints video images, frames, characters, and the like on a display medium such as paper.

The processing unit 20 includes one or more processors and its/their peripheral circuits. The processing unit 20 comprehensively controls the overall operation of the movement/rotation information generating apparatus 1, and is, for example, a central processing unit (CPU). The processing unit 20 executes processing based on programs (driver programs, operating system program, application programs, and the like) stored in the storage unit 11. The processing unit 20 may execute a plurality of programs (application programs and the like) in parallel.

The processing unit 20 includes a jaw scan data obtaining unit 21, a jaw image determining unit 22, a movement point identifying unit 23, a reference point obtaining unit 24, a movement/rotation information calculating unit 25, a movement/rotation information output unit 26, a reference position image generating unit 27, and a reference position image data output unit 28. The movement point identifying unit 23 includes a crown position estimating unit 231, a target tooth feature point extracting unit 232, a feature point clustering unit 233, and a movement point determining unit 234. These units are function modules realized by a program executed by a processor included in the processing unit 20. Alternatively, these units may be mounted as firmware on the movement/rotation information generating apparatus 1.

Figure 3:
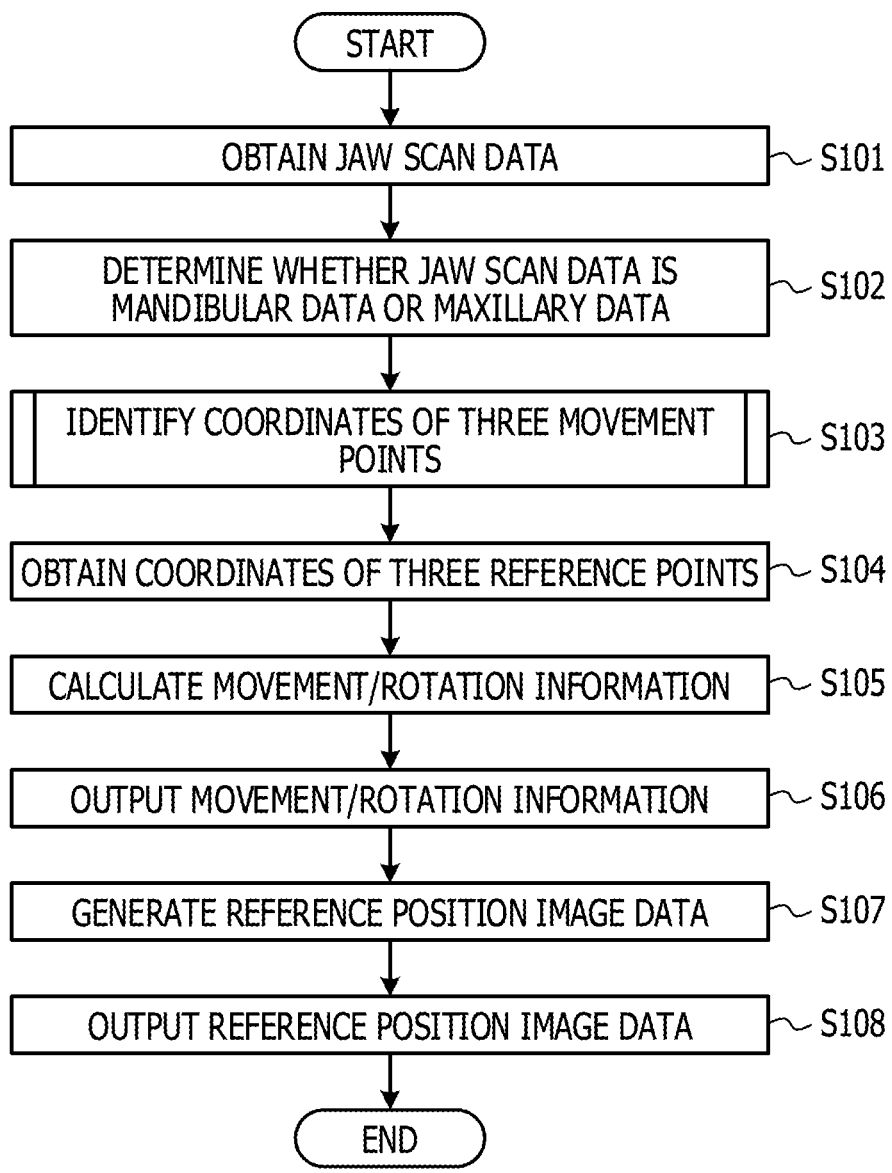
FIG. 3 is a flowchart of a movement/rotation information generating process performed by the movement/rotation information generating apparatus illustrated in FIG. 2.

FIG. 3 is a flowchart of a movement/rotation information generating process performed by the movement/rotation information generating apparatus 1. The movement/rotation information generating process illustrated in FIG. 3 is executed mainly by the processing unit 20 based on a program stored in advance in the storage unit 11, in cooperation with the elements of the movement/rotation information generating apparatus 1.

At first, the jaw scan data obtaining unit 21 obtains jaw scan data indicating the shape of each crown including a plurality of vertices (S101). Next, the jaw image determining unit 22 determines whether the obtained jaw scan data is mandibular scan data corresponding to a mandibular image including the mandible or maxillary scan data corresponding to a maxillary image including the maxilla, in accordance with a selection instruction given by a user (S102). The jaw image determining unit 22 determines whether the obtained jaw scan data is mandibular scan data or maxillary scan data in accordance with a selection instruction input via a graphical user interface (GUI) displayed on the output unit 13.

Next, the movement point identifying unit 23 identifies the coordinates of three movement points corresponding to at least three types of teeth included in a jaw image corresponding to the obtained jaw scan data (S103). The coordinates of movement points identified by the movement point identifying unit 23 are an example of position information on movement points.

Figure 4:
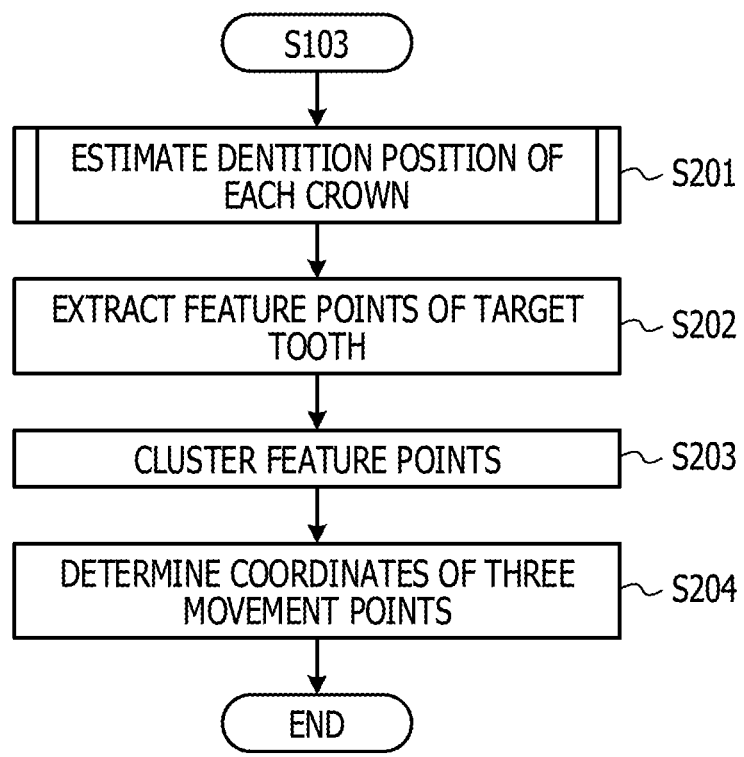
FIG. 4 is a flowchart illustrating a more detailed process of the processing in step S103.

FIG. 4 is a flowchart illustrating a more detailed process of the processing in step S103.

At first, the crown position estimating unit 231 estimates the dentition position of each crown included in the jaw scan data (S201).

Figure 5:
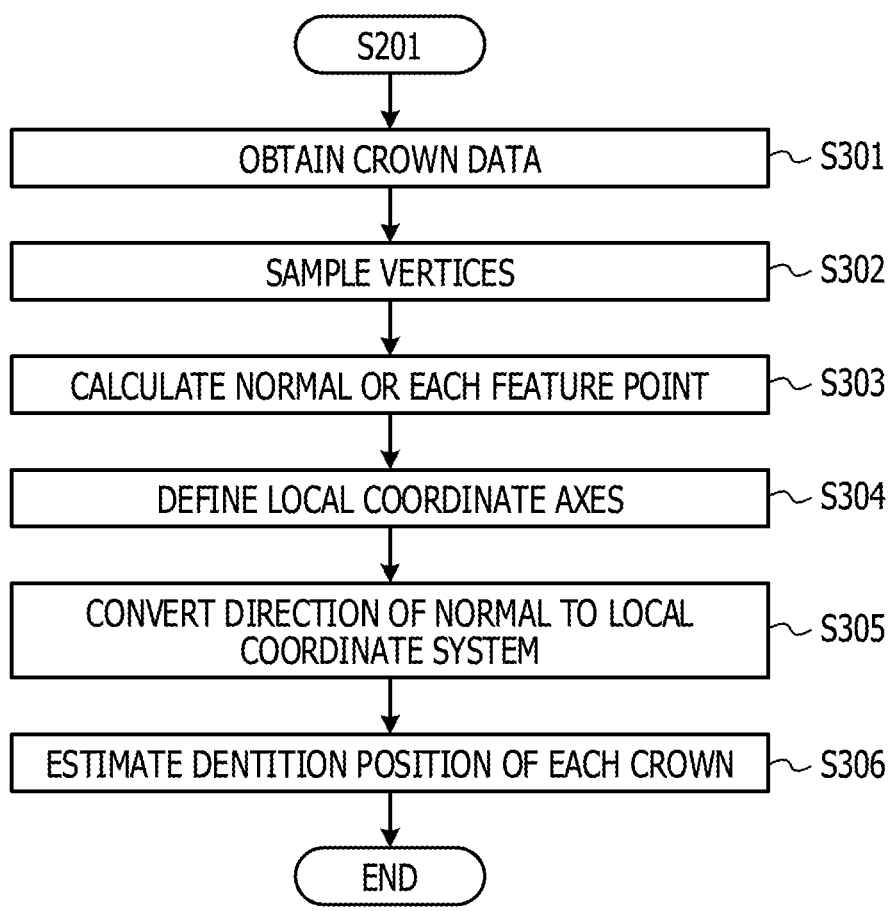
FIG. 5 is a flowchart illustrating a more detailed process of the processing in step S201.
Figure 6:
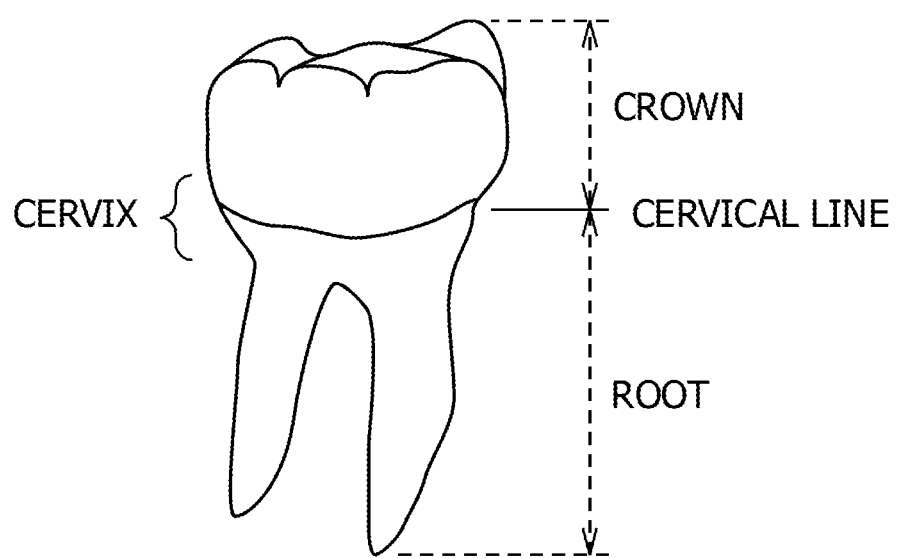
FIG. 6 is a perspective view of a tooth.
Figure 7B:
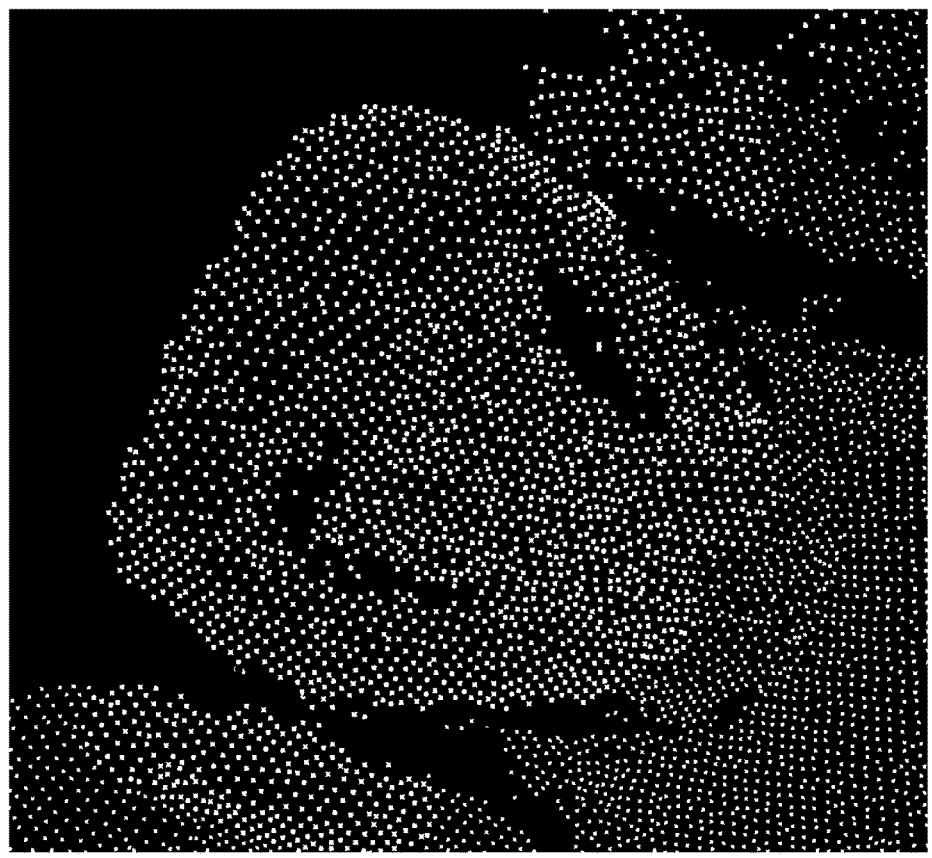
FIG. 7B is a diagram illustrating a 3D point group corresponding to the 3D surface mesh illustrated in FIG. 7A.
Figure 7A:
FIG. 7A is a diagram illustrating an example of a 3D surface mesh included in jaw scan data.

FIG. 5 is a flowchart illustrating a more detailed process of the processing in step S201. FIG. 6 is a perspective view of a tooth. FIG. 7A is a diagram illustrating an example of a 3D surface mesh included in the jaw scan data. FIG. 7B is a diagram illustrating a 3D point group corresponding to the 3D surface mesh illustrated in FIG. 7A.

At first, the crown position estimating unit 231 obtains crown data indicating the shape of each crown including a plurality of vertices (S301).

The crown is a part of a tooth, which is visible (erupted) in the mouth from the gum, and which is covered by enamel. A portion below the crown is referred to as a "root", and the boundary between the crown and the root is referred to as a "cervical line".

Jaw scan data 701 is obtained as tooth-form information of an unspecified number of people, and is obtained by a dental 3D scanner (not illustrated). In one example, the jaw scan data 701 is obtained as data for dental CAD and CAM software at dental lavatories, dental clinics, and the like. The jaw scan data 701 is stored in a file format such as stl, ply, off, or 3ds in the storage unit 11. The jaw scan data 701 is an aggregate of triangular polygons. 3D point group data 702 includes a plurality of vertices corresponding to the vertices of triangular polygons included in the jaw scan data 701.

Next, the crown position estimating unit 231 samples vertices included in an analysis target area of the jaw scan data 701 evenly, that is, uniformly, from the whole area of the aggregate (S302). In one example, the crown position estimating unit 231 samples about 200,000 to 600,000 vertices included in an analysis target area of the jaw scan data 701, and samples about 10,000 feature points. Here, the analysis target area is set to an area within a certain range from a target location for specifying the tooth type.

Figure 8:
FIG. 8 is a diagram illustrating an example of feature points sampled by a crown position estimating unit illustrated in FIG. 2.

FIG. 8 is a diagram illustrating an example of feature points sampled by the crown position estimating unit 231. Feature points are illustrated as black points in FIG. 9.

Next, the crown position estimating unit 231 calculates the normal of each of the feature points sampled in the processing in step S302 (S303). The crown position estimating unit 231 calculates the normal of each feature point by weighting the direction of the normal of each of triangular polygons including the feature point in accordance with the area of the respective polygons.

Figure 9:
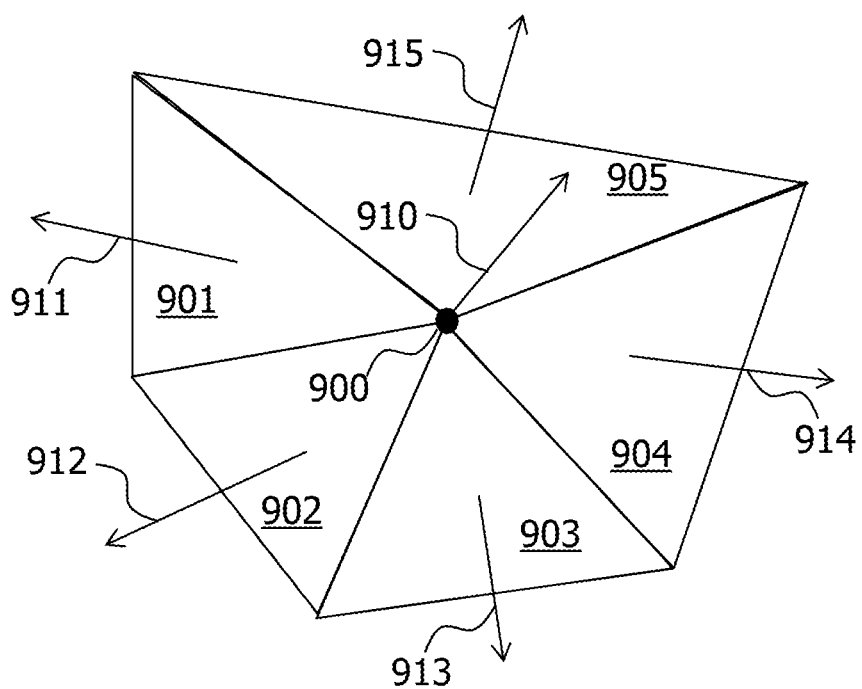
FIG. 9 is a diagram illustrating an example of a process of calculating the normal of a feature point.

FIG. 9 is a diagram illustrating an example of a process of calculating the normal of a feature point.

A feature point 900 is the vertex of five polygons, namely, a first polygon 901, a second polygon 902, a third polygon 903, a fourth polygon 904, and a fifth polygon 905. A first normal 911 is the normal of the first polygon 901. A second normal 912 is the normal of the second polygon 902. A third normal 913 is the normal of the third polygon 903. A fourth normal 914 is the normal of the fourth polygon 904. A fifth normal 915 is the normal of the fifth polygon 905. The first normal 911, the second normal 912, the third normal 913, the fourth normal 914, and the fifth normal 915 have an identical unit length.

The crown position estimating unit 231 calculates the direction of a normal 910 of the feature point 900 by weighting the first normal 911 to the fifth normal 915 according to the respective areas of the first polygon 901 to the fifth polygon 905. The normal 910 of the feature point 900 have a unit length, like the first normal 911 to the fifth normal 915.

Figure 10:
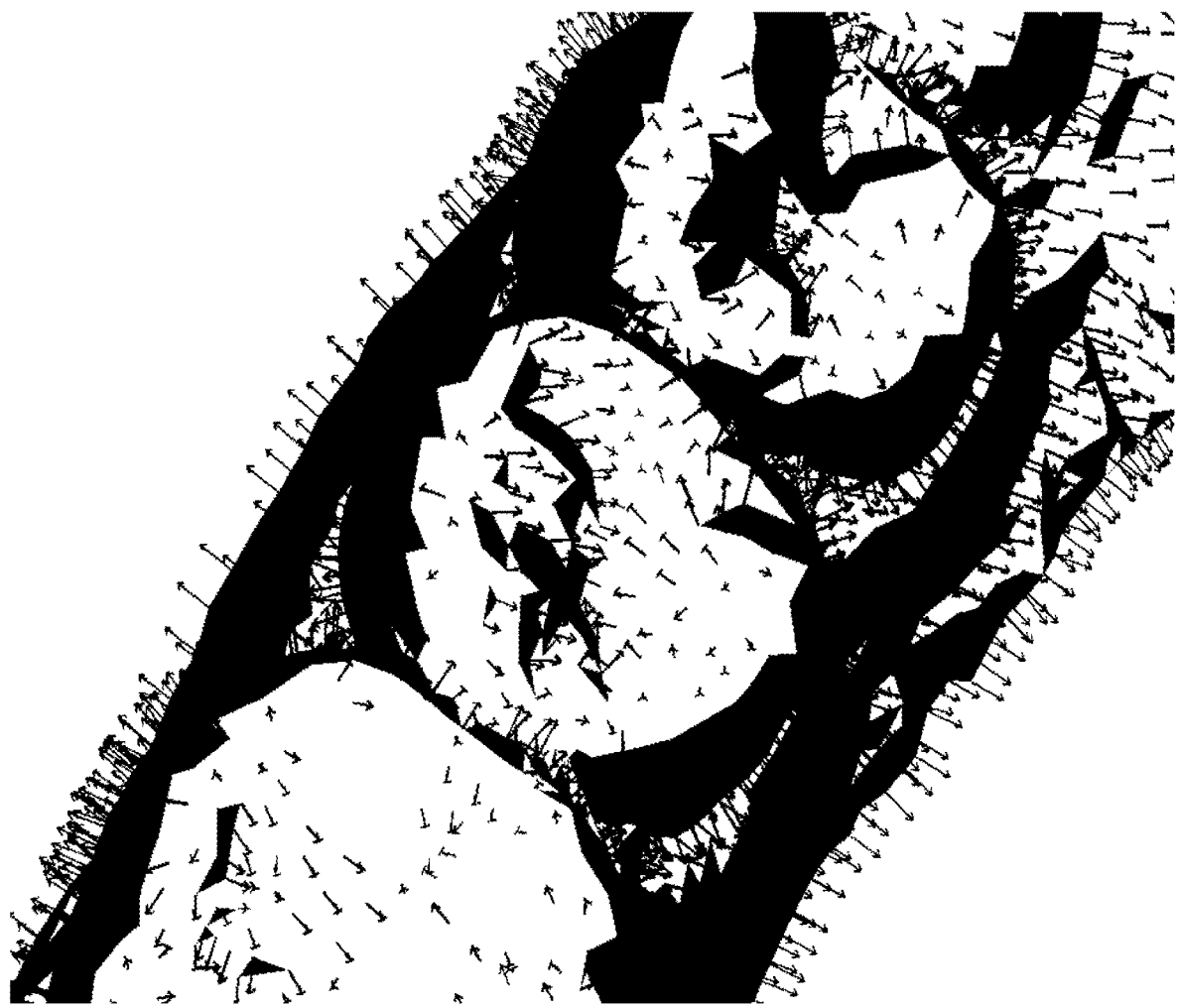
FIG. 10 is a diagram illustrating an example of the normal of each feature point, calculated in the processing in step S303.

FIG. 10 is a diagram illustrating an example of the normal of each feature point, calculated in the processing in step S303. The normal of each feature point calculated in the processing in step S303 is calculated by weighting the direction of the normal of each of triangular polygons including the feature point in accordance with the area of the respective polygons, and has an identical unit length.

Next, the crown position estimating unit 231 defines local coordinate axes for the plurality of feature points based on the distribution of the directions of the normals calculated in the processing in step S303 (S304). That is, the crown position estimating unit 231 calculates a local coordinate system based on the variance of the normals of a point group included in the analysis target area.

Figure 11:
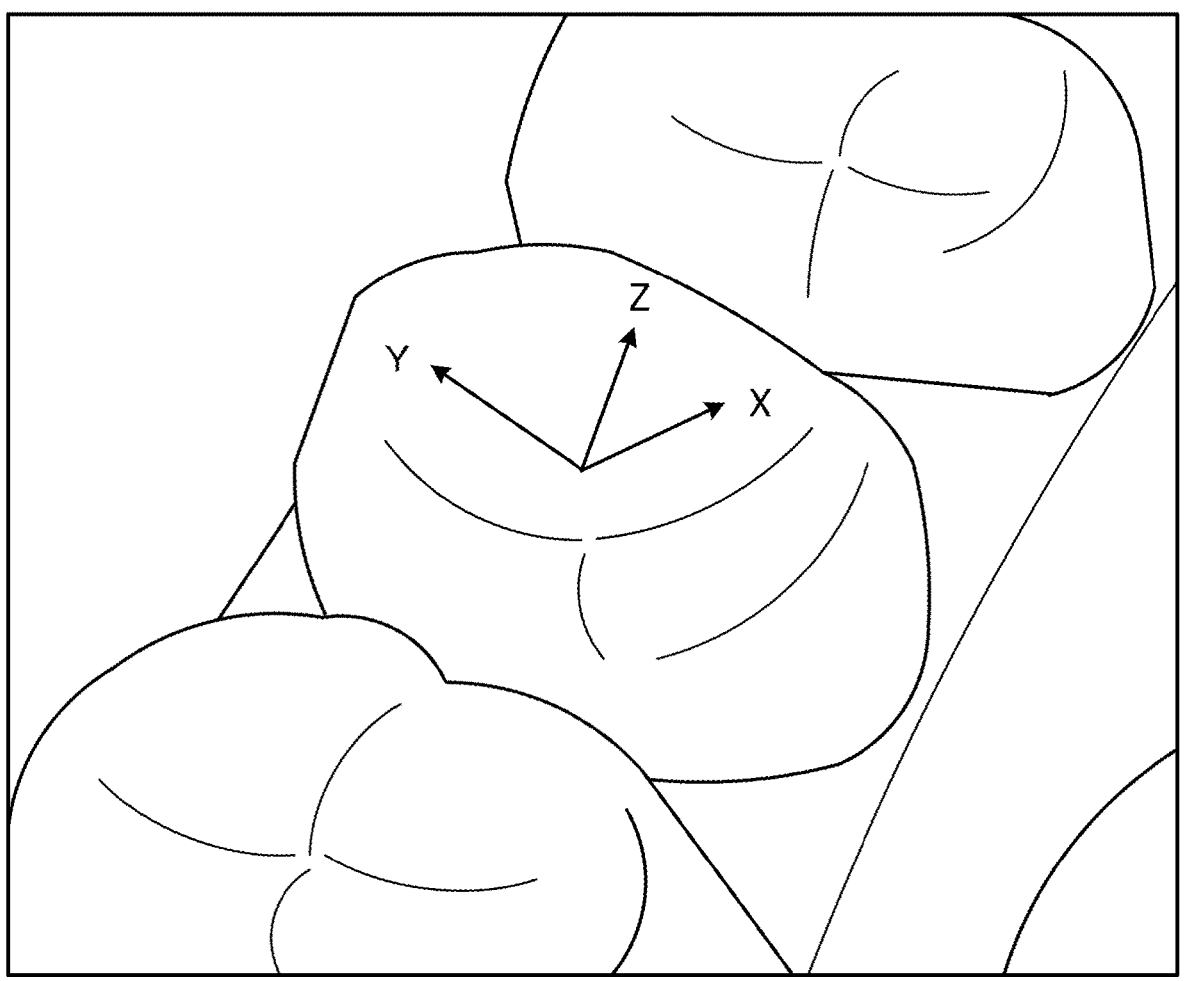
FIG. 11 is a diagram illustrating an example of a local coordinate system calculated in the processing in step S304.

FIG. 11 is a diagram illustrating an example of the local coordinate system (local reference frame (LRF)) calculated in the processing in step S304.

In the local coordinate system, the X direction where the X-axis extends is defined as a direction where the directions of the normals calculated in the processing in step S303 are dispersed most, that is, a direction where the variance is the greatest. The Y direction where the Y-axis extends is a direction orthogonal to the X direction. The Z direction where the Z-axis extends is a direction orthogonal to both the X direction and the Y direction. In one example, as described in Japanese Patent Application No. 2016-107358 and Japanese Patent Application No. 2016-107803, the Y direction is calculated from the cross product of the second-axis calculation-axis N extending in a direction where the variance of the directions of the calculated normals is smallest and the X-axis. That is, the Y-axis is a direction that is orthogonal to the X-axis and that is also orthogonal to the second-axis calculation-axis N.

Next, for each of the plurality of feature points, the crown position estimating unit 231 converts the direction of the normal of the feature point calculated in the processing in step S303 to the local coordinate system calculated in the processing in step S304 (S305). That is, the crown position estimating unit 231 obtains the distribution of the directions in the local coordinate system of normal unit vectors corresponding to the individual points of the point group included in the analysis target area.

Figure 12:
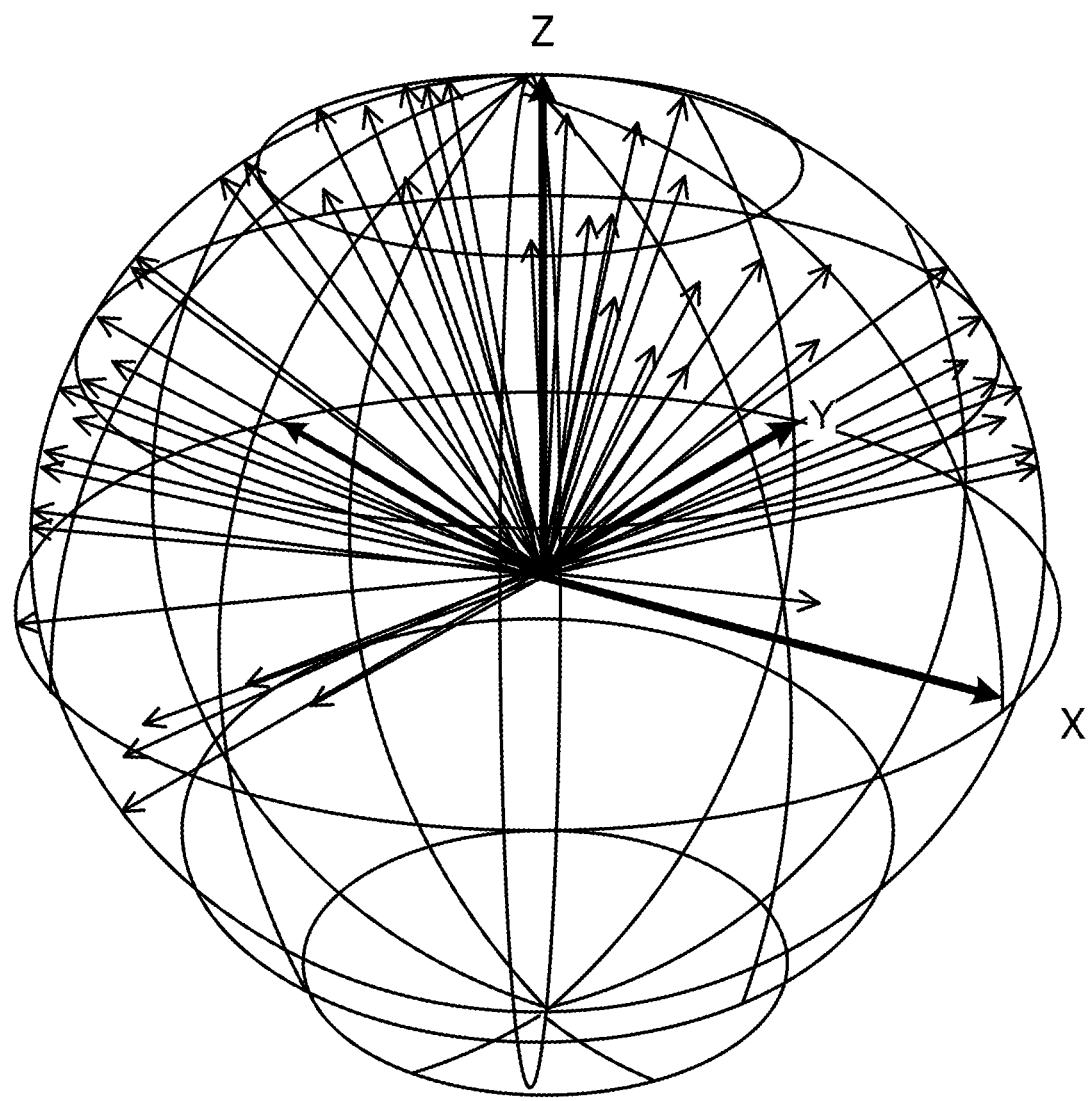
FIG. 12 is a histogram illustrating the direction of the normal of each feature point, which is converted to the polar coordinate system in the processing in step S305.

FIG. 12 is a histogram illustrating the direction of the normal of each of the feature points converted to the polar coordinate system in the processing in step S305. The histogram illustrated in FIG. 12 is also referred to as the Signature of Histograms of OrienTations (SHOT) descriptor.

Regarding the start point of the normal of each of the feature points calculated in the processing in step S303 as the origin, the crown position estimating unit 231 describes a histogram by spherically arranging the end point of the normal of each of the feature points, thereby describing a shape around each of the feature points.

Next, the crown position estimating unit 231 estimates crown position information indicating the dentition position of a tooth corresponding to each crown from the distribution of the directions of the normals of the feature points converted to the local coordinate system in the processing in step S305 (S306). That is, the crown position estimating unit 231 refers to the storage unit 11 storing distribution information of the directions in the local coordinate system of unit normal vectors corresponding to the individual points of the point group in association with the tooth type. The crown position estimating unit 231 estimates the tooth type corresponding to the obtained distribution as the tooth type in the analysis target area. If the jaw scan data 701 is determined as mandibular scan data in the processing in step S102, the crown position estimating unit 231 refers to distribution information of mandibular teeth. In contrast, if the jaw scan data 701 is determined as maxillary scan data in the processing in step S102, the crown position estimating unit 231 refers to distribution information of maxillary teeth. In one example, the dentition position of a tooth is a number represented by the Federation Dentaire Internationale (FDI) notation indicating the position of a tooth with a crown in the dentition.

Using machine learning, the crown position estimating unit 231 estimates crown position information indicating the position of the crown from the distribution of the directions of the normals of the feature points. When vector data of many numeric values is obtained, if there is a pattern there, the crown position estimating unit 231 learns that pattern. Based on the learned pattern, the crown position estimating unit 231 estimates the number represented by the FDI notation.

The function of the crown position estimating unit 231 to detect and identify, from jaw scan data, feature points belonging to a crown portion with a number represented by the FDI notation is generated in the following procedure (i) to (iii), for example:

(i) From a few thousand items of jaw scan data, obtain a two-dimensional histogram at the center position of a crown with a number represented by the FDI notation.

(ii) Have the crown position estimating unit 231 learn the association between the number represented by the FDI notation and the two-dimensional histogram.

(iii) Check that the crown position estimating unit 231, which has learned the association in (ii), has a certain detection capability.

Figure 13A:
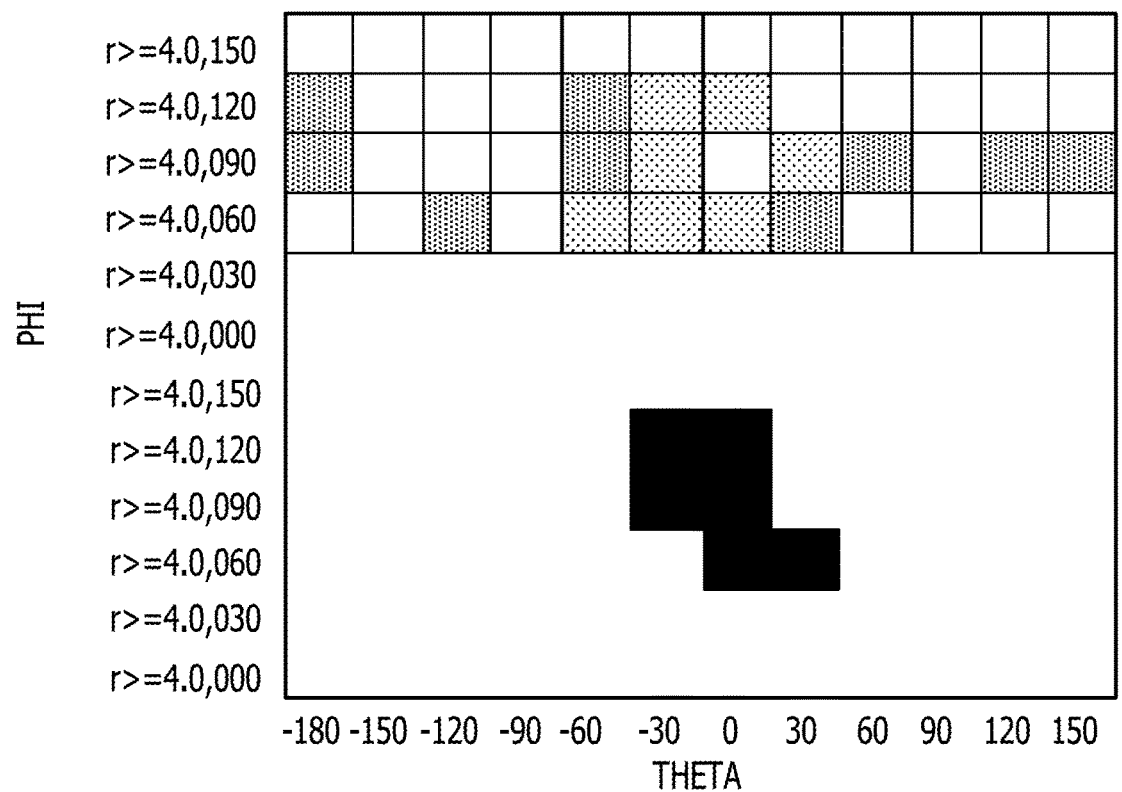
FIG. 13A is a diagram illustrating an example of a two-dimensional histogram.
Figure 13B:
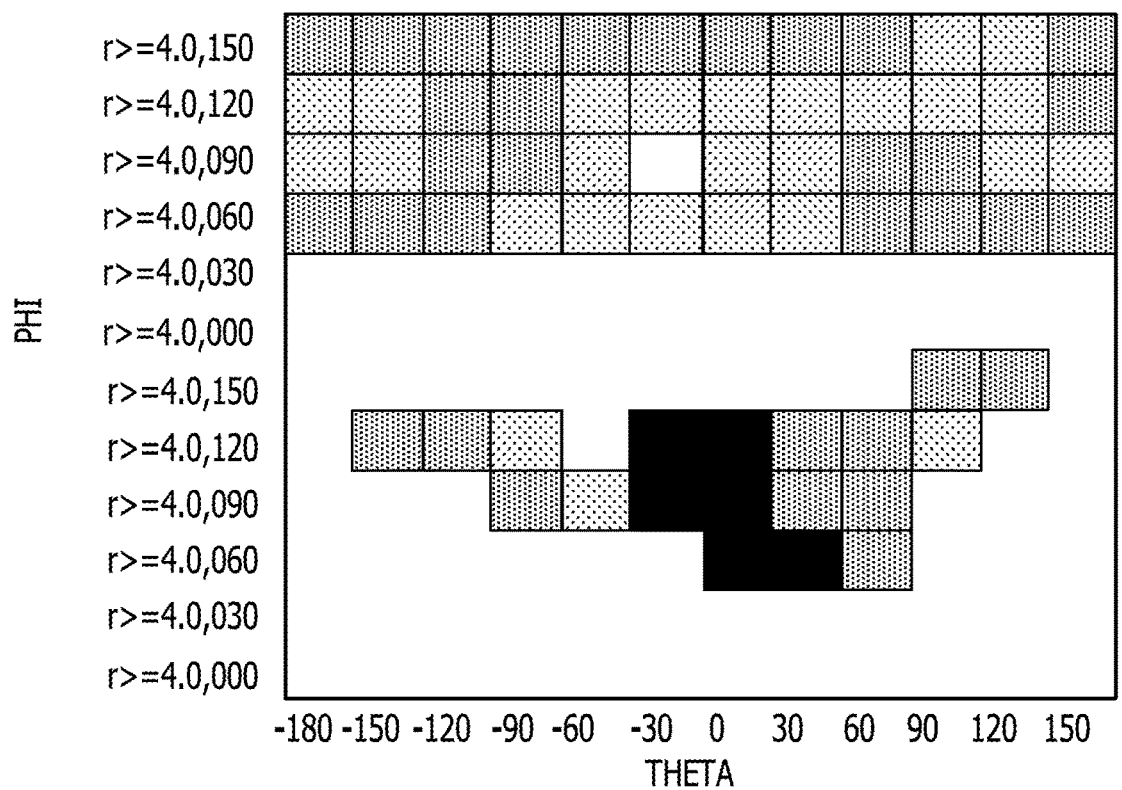
FIG. 13B is a diagram illustrating another example of a two-dimensional histogram.

FIG. 13A is a diagram illustrating an example of a two-dimensional histogram. FIG. 13B is a diagram illustrating another example of a two-dimensional histogram. In FIGS. 13A and 13B, the horizontal axis and the vertical axis represent arguments θ and ϕ in the polar coordinate system of the feature point converted in the processing in step S305.

FIG. 13A illustrates an example of a two-dimensional histogram corresponding to the number 11 represented by the FDI notation. FIG. 13B illustrates an example of a two-dimensional histogram corresponding to the number 14 represented by the FDI notation.

When the processing in step S201 ends, the target tooth feature point extracting unit 232 extracts feature points of target teeth of interest from the feature points of teeth sampled in the processing in step S302 in order to use the extracted feature points to identify three movement points (S202). When teeth used to identify three movement points are the left and right mandibular first teeth, the left mandibular sixth tooth, and the right mandibular sixth tooth, the target tooth feature point extracting unit 232 extracts feature points of the mandibular first teeth and the mandibular sixth teeth.

Next, the feature point clustering unit 233 clusters the feature points extracted in the processing in step S203 on a tooth-by-tooth basis (S203). In one example, the feature point clustering unit 233 classifies feature points that are distant by a certain threshold distance or greater into different clusters. The left and right teeth given the same number have substantially line symmetrical shapes. Therefore, it is not easy to determine whether each of feature points forming the left and right teeth that have the same number and that are included in a jaw image corresponding to jaw scan data is a feature point of the left or right tooth. The feature point clustering unit 233 classifies, based on a threshold distance that is longer than the width of the crown of each of the left and right teeth with the same number and that is shorter than the distance between the left and right teeth with the same number, feature points into left and right clusters, thereby clustering feature points forming the left and right teeth. For example, the feature point clustering unit 233 clusters, based on a threshold distance that is longer than the width of the crown of each of the mandibular sixth teeth and that is shorter than the distance between the left and right mandibular sixth teeth, feature points forming images of the left mandibular sixth tooth and the right mandibular sixth tooth. Because the left and right mandibular first teeth are adjacent to each other, the left and right mandibular first teeth may be treated as one tooth without clustering feature points forming images of the left mandibular first tooth and the right mandibular first tooth.

Next, the movement point determining unit 234 determines the coordinates of three movement points, namely, a first movement point to a third movement point based on the feature points clustered in the processing in step S203 (S204). In one example, the movement point determining unit 234 determines the coordinates of the center of gravity of feature points forming an image of the left and right mandibular first teeth as the coordinates of the first movement point. The movement point determining unit 234 determines the coordinates of the center of gravity of feature points forming an image of the left mandibular sixth tooth as the coordinates of the second movement point. The movement point determining unit 234 determines the coordinates of the center of gravity of feature points forming an image of the right mandibular sixth tooth as the coordinates of the third movement point. In another example, the movement point determining unit 234 determines the central coordinates of feature points forming an image of the left and right mandibular first teeth as the coordinates of the first movement point. The movement point determining unit 234 determines the central coordinates of feature points forming an image of the left mandibular sixth tooth as the coordinates of the second movement point. The movement point determining unit 234 determines the central coordinates of feature points forming an image of the right mandibular sixth tooth as the coordinates of the third movement point.

When the processing in step S103 ends, the reference point obtaining unit 24 obtains the coordinates of three reference points, namely, a first reference point to a third reference point, indicating the reference positions respectively of at least three types of teeth (S104). The first to third reference points are points that are not related at all to the jaw scan data obtained in the processing in step S101. In one example, the first to third reference points may be obtained from jaw data of a standard model placed at a standard position. In another example, the first to third reference points may be defined in advance by an apparatus and system, for example, where the movement/rotation information generating program is installed. In one example, the coordinates of the first reference point are the coordinates of the center of gravity of the left and right mandibular first teeth of a mandibular reference image serving as a reference. The coordinates of the second reference point are the coordinates of the center of gravity of the left mandibular sixth tooth of a mandibular reference image serving as a reference. The coordinates of the third reference point are the coordinates of the center of gravity of the right mandibular sixth tooth of a mandibular reference image serving as a reference. In another example, the coordinates of the first reference point are the central coordinates of the left and right mandibular first teeth of a mandibular reference image serving as a reference. The coordinates of the second reference point are the central coordinates of the left mandibular sixth tooth of a mandibular reference image serving as a reference. The coordinates of the third reference point are the central coordinates of the right mandibular sixth tooth of a mandibular reference image serving as a reference. The coordinates of the first to third reference points are stored in the storage unit 11 as positional relationship information associating the tooth types and the positional relationship.

Next, the movement/rotation information calculating unit 25 calculates movement/rotation information indicating a movement amount and a rotation amount of a movement surface formed by the first to third movement points when matching the movement surface to a reference surface formed by the first to third reference points (S105). More specifically, the movement/rotation information calculating unit 25 calculates movement/rotation information so as to match the first movement point 101 to the first reference point 111, the second movement point 102 to the second reference point 112, and the third movement point 103 to the third reference point 113. In one example, the movement/rotation information may be information indicating parallel movement and rotation by affine transformation. The movement/rotation information may be a matrix indicating the movement amount and rotation amount of the movement surface when matching the movement surface to the reference surface.

In one example, at first, the movement/rotation information calculating unit 25 moves the movement surface so as to match the center of gravity of a triangle formed by the first to third movement points to the center of gravity of a triangle formed by the first to third reference points. Next, the movement/rotation information calculating unit 25 rotates the movement surface around the center of gravity of the triangle formed by the first to third movement points so as to match the movement surface to the reference surface. The movement/rotation information calculating unit 25 rotates in a plane the first to third reference points on the reference surface such that the sum of the offset distances between the first to third movement points and the first to third reference points becomes minimum. The sum of the offset distances between the first to third movement points and the first to third reference points is, in one example, calculated using the least squares method of the distances between the first to third moving points and the first to third reference points.

The size of the mandible included in a mandibular image corresponding to scan data obtained by a dental 3D scanner device changes in accordance with the size of the mandible of a patient whose mandible has been scanned. Therefore, not all the first to third movement points completely match the first to third reference points. To match the first to third movement points to the first to third reference points as completely as possible, the movement/rotation information calculating unit 25 moves/rotates the first to third movement points such that the sum of the offset distances between the first to third movement points and the first to third reference points becomes minimum.

Next, the movement/rotation information output unit 26 outputs the calculated movement/rotation information (S106).

Next, the reference position image generating unit 27 generates reference position image data indicating a reference position image where a jaw image corresponding to jaw scan data is moved and/or rotated based on the movement/rotation information (S107). The reference position information may be an image obtained by moving a jaw image corresponding to jaw scan data. The reference position information may be an image obtained by rotating a jaw image corresponding to jaw scan data. The reference position information may be an image obtained by moving and rotating a jaw image corresponding to jaw scan data.

The reference position image data output unit 28 outputs the reference image data generated in the processing in step S107 (S108).

The movement/rotation information generating apparatus 1 calculates movement/rotation information indicating a movement amount and a rotation amount of a movement surface formed by three movement points when matching the movement surface to a reference surface formed by three reference points, thereby moving a jaw image in a desired direction and to a desired position and displaying the moved jaw image.

The movement/rotation information generating apparatus 1 can generate reference position image data indicating a reference position image obtained by moving and/or rotating a jaw image based on movement/rotation information. A reference position image corresponding to reference position image data generated by the movement/rotation information generating apparatus 1 is applicable to various application programs of virtual articulators and the like.

Figure 14:
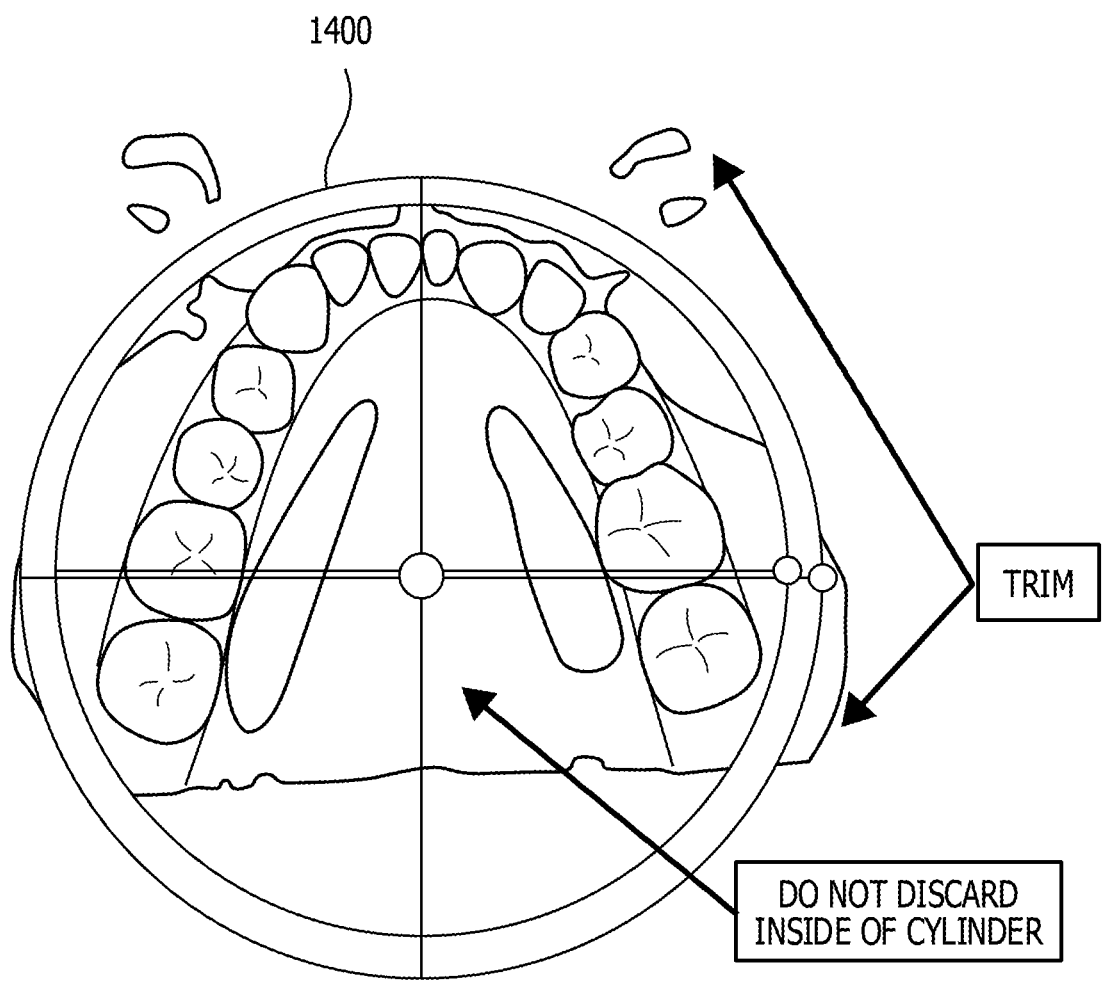
FIG. 14 is a diagram illustrating an example of a scan range specified by the scanner device.

Using a reference position image corresponding to reference position image data generated by the movement/rotation information generating apparatus 1, a scan range to be scanned by a dental 3D scanner can be defined. In the case of scanning a tooth-form model with the use of a model scanner, there is a scanner device that specifies a scan range 1400 illustrated in FIG. 14 in accordance with the result of a first rough scan in order to reduce the size of scan data. A reference position image corresponding to reference position mage data generated by the movement/rotation information generating apparatus 1 is used, and the positions of anterior teeth and posterior teeth are estimated. Accordingly, a scan range including anterior teeth and posterior teeth can be automatically specified.

The movement/rotation information generating apparatus 1 is applied to tooth-form scan data stored in an electronic archive at an orthodontic clinic and the like. Accordingly, the directions of tooth-form images corresponding to items of tooth-form scan data stored in the electronic archive can be made identical to one another. When the movement/rotation information generating apparatus 1 is applied to tooth-form scan data stored in the electronic archive, the directions of tooth-form images stored in the electronic archive are made identical to one another, thereby making it easier to organize the tooth-form scan data and to visually recognize the tooth-form images.

The movement/rotation information generating apparatus 1 clusters, according to tooth type, point groups that are included in jaw scan data and that are associated with respective tooth types, thereby classifying point groups forming images including the left and right teeth having the same number and symmetrical shapes. At this time, the movement/rotation information generating apparatus 1 clusters, among point groups, points according to the distance between points associated with any tooth type. In one example, the movement/rotation information generating apparatus 1 classifies feature points into left and right clusters based on a threshold distance that is longer than the width of the crown of each of the left and right teeth having the same number and that is shorter than the distance between the left and right teeth having the same number.

The movement/rotation information generating apparatus 1 determines whether the jaw scan data is mandibular scan data or maxillary scan data in accordance with a user's selection instruction. However, the movement/rotation information generating apparatus 1 according to the embodiment may alternatively determine whether the obtained jaw scan data is mandibular scan data or maxillary scan data based on the jaw scan data. For example, the movement/rotation information generating apparatus 1 according to the embodiment may determine, from the obtained scan data, whether the jaw scan data is mandibular scan data or maxillary scan data based on whether the third tooth has a crown shape corresponding to the so-called double tooth.

The movement/rotation information generating apparatus 1 executes a movement/rotation information generating process using the left and right mandibular first teeth, the left mandibular sixth tooth, and the right mandibular sixth tooth. However, the movement/rotation information generating apparatus 1 according to the embodiment may execute a movement/rotation information generating process using other teeth. For example, the movement/rotation information generating apparatus 1 according to the embodiment may execute a movement/rotation information generating process using the left mandibular seventh tooth and the right mandibular seventh tooth instead of the left mandibular sixth tooth and the right mandibular sixth tooth. The movement/rotation information generating apparatus 1 according to the embodiment may execute a movement/rotation information generating process using the left mandibular seventh tooth and the right mandibular seventh tooth in addition to the left and right mandibular first teeth, the left mandibular sixth tooth, and the right mandibular sixth tooth.

FIG. 15 is a diagram for describing an example that uses the left and right mandibular first teeth, mandibular sixth teeth, and mandibular seventh teeth in the case of executing a movement/rotation information generating process.

The movement/rotation information generating apparatus 1 according to the embodiment determines the coordinates of the center of gravity of the left and right mandibular first teeth as the coordinates of a first movement point. The movement/rotation information generating apparatus 1 determines the coordinates of the center of gravity of the left mandibular sixth tooth and mandibular seventh tooth as the coordinates of a second movement point, and determines the coordinates of the center of gravity of the right mandibular sixth tooth and mandibular seventh tooth as the coordinates of a third movement point. The movement/rotation information generating apparatus 1 according to the embodiment executes a movement/rotation information generating process using two teeth, namely, a mandibular sixth tooth and a mandibular seventh tooth. In doing so, the number of feature points to use increases. Accordingly, the accuracy of the movement/rotation information generating process is improved.

The movement/rotation information generating apparatus 1 according to the embodiment may determine the coordinates of a reference surface as arbitrary coordinates.

Figure 16B:
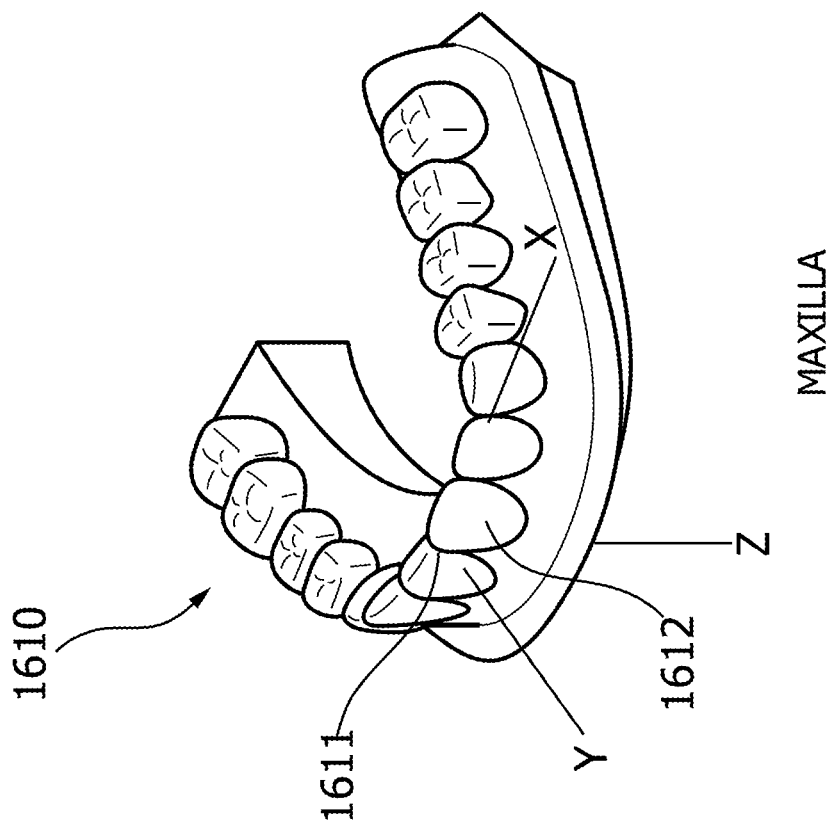
FIG. 16B is a diagram illustrating an example of the coordinate axes of a maxillary reference surface.
Figure 16A:
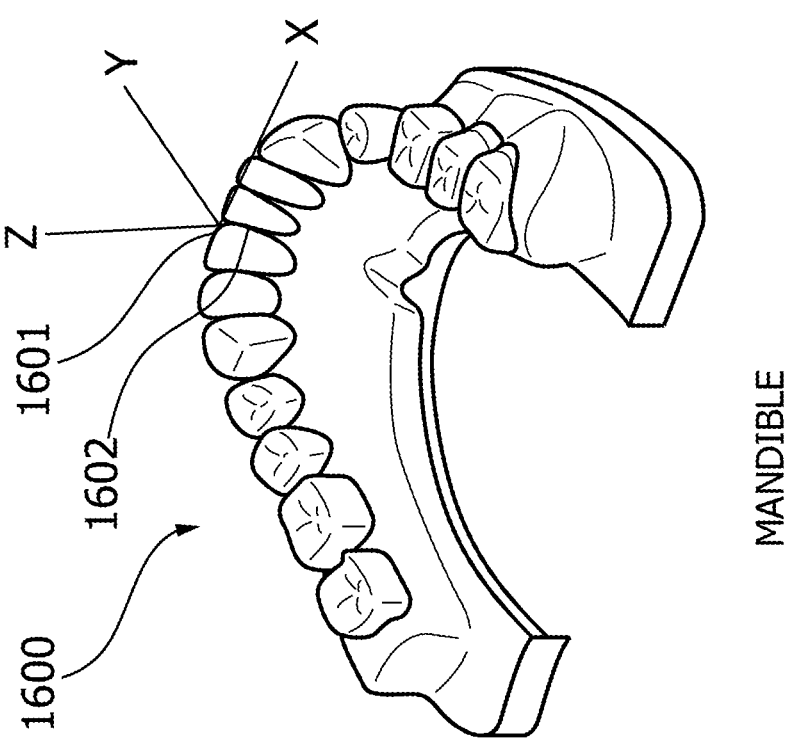
FIG. 16A is a diagram illustrating an example of the coordinate axes of a mandibular reference surface.

FIG. 16A is a diagram illustrating an example of the coordinate axes of a mandibular reference surface. FIG. 16B is a diagram illustrating an example of the coordinate axes of a maxillary reference surface.

The coordinate axes of the mandibular reference surface may have the coordinates of the center of gravity of the crowns of a left mandibular first tooth 1601 and a right mandibular first tooth 1602 in a mandibular image 1600 as the origin. Of the coordinate axes of the mandibular reference surface, the X-axis may be extended in the rightward direction of the mandibular image 1600, the Y-axis may be extended in the frontward direction of the mandibular image 1600, and the Z-axis may be extended in the upward direction of the mandibular image 1600. In contrast, the coordinate axes of the maxillary reference surface may have the coordinates of the center of gravity of the crowns of a left maxillary first tooth 1611 and a right maxillary first tooth 1612 in a maxillary image 1610 as the origin. Of the coordinate axes of the maxillary reference surface, the X-axis may be extended in the leftward direction of the maxillary image 1610, the Y-axis may be extended in the frontward direction of the maxillary image 1610, and the Z-axis may be extended in the downward direction of the maxillary image 1610. The movement/rotation information generating apparatus 1 according to the embodiment may define the coordinate axes of the maxillary reference surface and the coordinate axes of the mandibular reference surface so as to match each other. By matching the coordinate axes of the maxillary reference surface and the mandibular reference surface with each other, it becomes easier for the movement/rotation information generating apparatus 1 according to the embodiment to perform initial alignment when determining the occlusal state of the maxilla and the mandible. By matching the coordinate axes of the maxillary reference surface and the mandibular reference surface with each other, it becomes easier to apply the movement/rotation information generating apparatus 1 according to the embodiment to various application programs of virtual articulators and the like.

Figure 17:
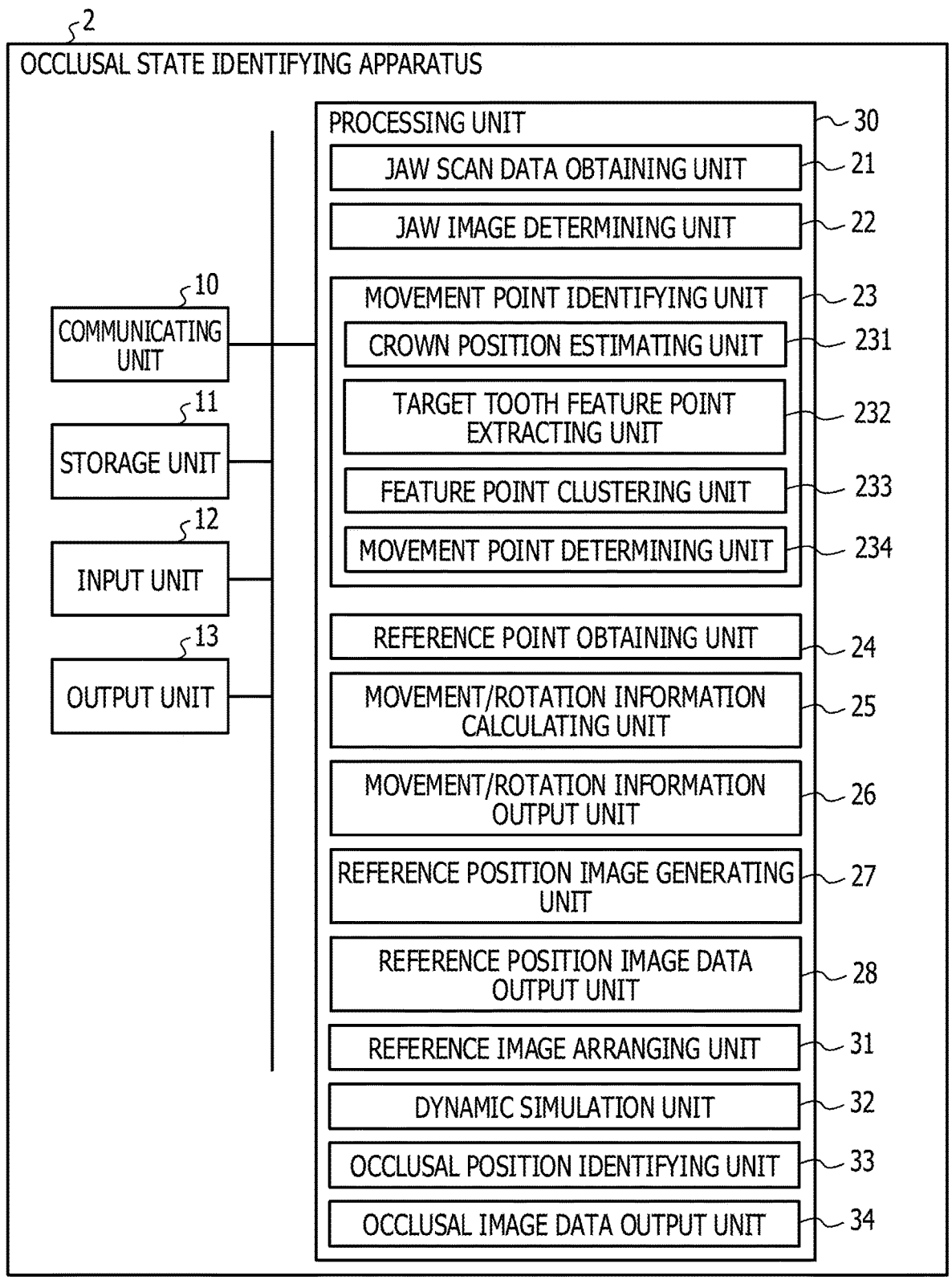
FIG. 17 is a block diagram of an occlusal state identifying apparatus according to the embodiment.

FIG. 17 is a block diagram of an occlusal state identifying apparatus according to the embodiment.

An occlusal state identifying apparatus 2 is different from the movement/rotation information generating apparatus 1 in the point that the occlusal state identifying apparatus 2 includes a processing unit 30 instead of the processing unit 20. The processing unit 30 is different from the processing unit 20 in the point that the processing unit 30 includes a reference image arranging unit 31, a dynamic simulation unit 32, an occlusal position identifying unit 33, and an occlusal image data output unit 34. Because the configurations and functions of the elements of the occlusal state identifying apparatus 2 except for the reference image arranging unit 31 to the occlusal image data output unit 34 are the same as or similar to the configurations and functions of the movement/rotation information generating apparatus 1 having the same reference numerals, detailed descriptions are omitted here.

FIG. 18 is a flowchart of an occlusal state identifying process performed by the occlusal state identifying apparatus 2. The movement/rotation information generating process illustrated in FIG. 18 is executed mainly by the processing unit 30 based on a program stored in advance in the storage unit 11, in cooperation with the elements of the occlusal state identifying apparatus 2.

At first, the jaw scan data obtaining unit 21 obtains maxillary scan data corresponding to a maxillary image including the maxilla (S401). Next, the jaw image determining unit 22 determines that, in accordance with a user's selection instruction, the obtained maxillary scan data is maxillary scan data corresponding to a maxillary image including the maxilla (S402). Next, the jaw scan data obtaining unit 21 obtains mandibular scan data corresponding to a mandibular image including the mandible (S403). Next, the jaw image determining unit 22 determines that, in accordance with a user's selection instruction, the obtained mandibular scan data is mandibular scan data corresponding to a mandibular image including the mandible (S404).

Next, the movement point identifying unit 23, the reference point obtaining unit 24, and the movement/rotation information calculating unit 25 calculate maxillary movement/rotation information indicating a movement amount and a rotation amount of a maxillary movement surface of the maxillary image corresponding to the obtained maxillary scan data when matching the maxillary movement surface to a maxillary reference surface (S405). Next, the movement point identifying unit 23, the reference point obtaining unit 24, and the movement/rotation information calculating unit 25 calculate mandibular movement/rotation information indicating a movement amount and a rotation amount of a mandibular movement surface of the mandibular image corresponding to the obtained mandibular scan data when matching the mandibular movement surface to a mandibular reference surface (S406). Because the processing in steps S405 and S406 is the same as or similar to the processing in steps S103 to S105, a detailed description thereof is omitted here.

Next, the reference image arranging unit 31 arranges based on the maxillary movement/rotation information calculated in the processing in step S405, the maxillary image at a certain maxillary reference position by moving/rotating the maxillary image such that the maxillary movement surface of the maxillary image matches the maxillary reference surface (S407). Next, the reference image arranging unit 31 arranges based on the mandibular movement/rotation information calculated in the processing in step S406, the mandibular image at a certain mandibular reference position by moving/rotating the mandibular image such that the mandibular movement surface of the mandibular image matches the mandibular reference surface (S408).

The maxillary movement surface of the maxillary image matches the maxillary reference surface, and the mandibular movement surface of the mandibular image matches the mandibular reference surface. Therefore, the maxilla included in the maxillary image and the mandible included in the mandibular image are arranged to be separated from each other such that the corresponding teeth oppose each other. In one example, the X coordinate and the Y coordinate of the coordinates of the center of gravity of the left and right maxillary first teeth included in the maxillary image match the X coordinate and the Y coordinate of the coordinates of the center of gravity of the left and right mandibular first teeth included in the mandibular image. The X coordinate and the Y coordinate of the coordinates of the center of gravity of the left maxillary sixth tooth included in the maxillary image match the X coordinate and the Y coordinate of the coordinates of the center of gravity of the left mandibular sixth tooth included in the mandibular image. Furthermore, the X coordinate and the Y coordinate of the coordinates of the center of gravity of the right maxillary sixth tooth included in the maxillary image match the X coordinate and the Y coordinate of the coordinates of the center of gravity of the right mandibular sixth tooth included in the mandibular image.

Next, the dynamic simulation unit 32 executes a moving process of moving the maxilla included in the maxillary image by executing a dynamic simulation (S409). In response to execution of a dynamic simulation by the dynamic simulation unit 32, with respect to the mandible which is fixed, the maxilla moves until the maxilla contacts the mandible and stops. A dynamic simulation is a simulation of calculating the motion of an object according to the laws of physics. A dynamic simulation does not move an object by directly moving an image representing the object, but calculates the motion of the object by indirectly moving the object through application of force such as gravity or tension. In one example, the dynamic simulation unit 32 executes a dynamic simulation to cause the maxilla included in the maxillary image to fall naturally due to gravity. The dynamic simulation unit 32 defines the maxilla included in the maxillary image as a substance having a uniform mass per unit surface area, and causes the maxilla included in the maxillary image to fall naturally due to gravity. That is, for the dynamic simulation unit 32, items of jaw scan data representing the maxillary image and the mandibular image are rigid bodies that are as thin as possible and that have a uniform thickness, like shell data such as shell elements of the finite element method or the like. The maxilla and the mandible are defined as rigid bodies having a uniform mass per unit surface area. The dynamic simulation unit 32 defines both the maxilla included in the maxillary image and the mandible included in the mandibular image as rigid bodies whose shapes are not deformed.

The dynamic simulation unit 32 executes a dynamic simulation by not taking into consideration the friction between maxillary teeth included in the maxillary image and mandibular teeth included in the mandibular image. That is, the dynamic simulation unit 32 executes a dynamic simulation by making the frictional force between maxillary teeth included in the maxillary image and mandibular teeth included in the mandibular image zero by making, for example, a friction coefficient between the maxillary teeth and the mandibular teeth zero.

Next, the occlusal position identifying unit 33 identifies the positional relationship between the maxillary image and the mandibular image after the moving process as a positional relationship corresponding to an occlusal state of the maxillary teeth included in the maxillary image and the mandibular teeth included in the mandibular image (S410). The occlusal position identifying unit 33 generates occlusal image data indicating an occlusal image including the maxillary image and the mandibular image identified as having a positional relationship corresponding to an occlusal state. The occlusal position identifying unit 33 stores the generated occlusal image data in the storage unit 11.

The occlusal image data output unit 34 outputs the occlusal image data generated in the processing in step S410 (S411).

By executing a dynamic simulation, the occlusal state identifying apparatus 2 moves at least one of the maxilla and the mandible, which are respectively included in the maxillary image and the mandibular image arranged such that the corresponding teeth oppose each other, thereby generating an occlusal image. The occlusal state identifying apparatus 2 generates an occlusal image by moving at least one of the maxilla and the mandible through execution of a dynamic simulation. That is, the occlusal state identifying apparatus 2 can generate an occlusal image without using scan data indicating an occlusal state.

The occlusal state identifying apparatus 2 executes a dynamic simulation by not taking into consideration the friction between the maxillary teeth included in the maxillary image and the mandibular teeth included in the mandibular image. Accordingly, a positional relationship in accordance with the shapes of the crowns of the maxillary teeth and the mandibular teeth can be identified as an occlusal state.

The occlusal state identifying apparatus 2 causes the maxilla included in the maxillary image to fall naturally, thereby bringing the maxillary teeth included in the maxillary image and the mandibular teeth included in the mandibular image into occlusion. However, the occlusal state identifying apparatus 2 according to the embodiment may alternatively move either the maxilla or the mandible according to the laws of physics. For example, the occlusal state identifying apparatus 2 according to the embodiment may turn the arrangement relationship between the maxillary image and the mandibular image upside down, cause the mandible included in the mandibular image to fall naturally due to gravity, and bring the maxillary teeth included in the maxillary image and the mandibular teeth included in the mandibular image into occlusion. At this time, with respect to the maxilla which is fixed, the mandible moves until the mandible contacts the maxilla and stops. The occlusal state identifying apparatus 2 according to the embodiment may move both the maxilla and the mandible by applying force to both the maxilla and the mandible in a direction in which the maxilla occludes with the mandible, thereby bringing the maxillary teeth included in the maxillary image and the mandibular teeth included in the mandibular image into occlusion.

The occlusal state identifying apparatus 2 identifies the arrangement relationship by making the frictional force between the maxillary teeth and the mandibular teeth zero. However, the occlusal state identifying apparatus 2 according to the embodiment may alternatively identify the arrangement relationship by making the frictional force between the maxillary teeth and the mandibular teeth substantially zero.

The occlusal state identifying apparatus 2 outputs occlusal image data indicating an occlusal image including the maxillary image and the mandibular image. However, the occlusal state identifying apparatus 2 according to the embodiment may alternatively output, in addition to the occlusal image data, movement/rotation information indicating a movement amount and/or a rotation amount of the mandible and/or the maxilla moved by executing a dynamic simulation. In this case, the occlusal state identifying apparatus 2 according to the embodiment includes a movement/rotation information output unit that outputs a movement amount and/or a rotation amount of the mandible and/or the maxilla moved by executing a dynamic simulation. The movement/rotation information output by the occlusal state identifying apparatus 2 according to the embodiment may include a matrix indicating a movement amount and/or a rotation amount of the mandible and/or the maxilla moved by executing a dynamic simulation.

The occlusal state identifying apparatus 2 executes processing using an image corresponding to scan data generated by a 3D scanner device. However, the occlusal state identifying apparatus 2 according to the embodiment may alternatively execute processing using an image corresponding to data other than scan data.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiment of the present invention has been described in detail, it should be understood that the various changes, substitutions, and alterations could be made hereto without departing from the spirit and scope of the invention.

What is claimed is:

1. An occlusal state identifying method executed by a processor included in an occlusal state identifying apparatus, the occlusal state identifying method comprising:
    obtaining maxillary shape data and mandibular shape data;
    arranging a maxillary image including a plurality of maxillary teeth corresponding to the obtained maxillary shape data and a mandibular image including a plurality of mandibular teeth corresponding to the obtained mandibular shape data such that a center of gravity of corresponding predetermined teeth match each other;
    defining a state where maxillary teeth included in the maxillary image, which has fallen naturally, collide with mandibular teeth included in the mandibular image and stop, by executing a dynamic simulation based on the arranged maxillary image and the arranged mandibular image; and
    identifying a positional relationship between the maxillary image and the mandibular image obtained by the defined state as a positional relationship corresponding to an occlusal state of the maxillary teeth included in the maxillary image and the mandibular teeth included in the mandibular image.

2. The occlusal state identifying method according to claim 1, further comprising
    outputting an occlusal image including the maxillary image and the mandibular image arranged respectively in the positional relationship between the maxillary image and the mandibular image after the moving process.

3. The occlusal state identifying method according to claim 1,
    wherein the maxillary shape data and the mandibular shape data are scan data generated by a 3D scanner device.

4. The occlusal state identifying method according to claim 1, wherein the defining includes
    moving the maxillary image, where the mandibular image is fixed, until the maxillary image contacts and stops on the mandibular image.

5. The occlusal state identifying method according to claim 1, wherein the defining includes
    moving the mandibular image, where the mandibular image is fixed, until the maxillary image contacts and stops on the mandibular image.

6. The occlusal state identifying method according to claim 1,
    wherein the dynamic simulation is executed under a condition where a frictional force between the mandibular image and the maxillary image is substantially zero.

7. The occlusal state identifying method according to claim 1, further comprising
    outputting movement/rotation information indicating a movement amount and/or a rotation amount of the mandibular image and/or the maxillary image moved by executing the dynamic simulation.

8. An occlusal state identifying apparatus comprising:
    a memory; and
    a processor coupled to the memory and configured to:
        obtain maxillary shape data and mandibular shape data,
        arrange a maxillary image including a plurality of maxillary teeth corresponding to the obtained maxillary shape data and a mandibular image including a plurality of mandibular teeth corresponding to the obtained mandibular shape data such that corresponding a center of gravity of corresponding predetermined teeth match each other,
        define a state where maxillary teeth included in the maxillary image, which has fallen naturally, collide with mandibular teeth included in the mandibular image and stop, by executing a dynamic simulation based on the arranged maxillary image and the arranged mandibular image, and
        identify a positional relationship between the maxillary image and the mandibular image obtained by the defined state as a positional relationship corresponding to an occlusal state of the maxillary teeth included in the maxillary image and the mandibular teeth included in the mandibular image.

9. The occlusal state identifying apparatus according to claim 8, wherein the processor is configured to
    output an occlusal image including the maxillary image and the mandibular image arranged respectively in the positional relationship between the maxillary image and the mandibular image after the moving process.

10. The occlusal state identifying apparatus according to claim 8,
    wherein the maxillary shape data and the mandibular shape data are scan data generated by a 3D scanner device.

11. The occlusal state identifying apparatus according to claim 8, wherein the processor is configured to
    move the maxillary image until the maxillary image contacts the mandibular image which is fixed and stops.

12. The occlusal state identifying apparatus according to claim 8, wherein the processor is configured to
    move the mandibular image until the mandibular image contacts the maxillary image which is fixed and stops.

13. The occlusal state identifying apparatus according to claim 8, wherein the dynamic simulation is executed under a condition where a frictional force between the mandibular image and the maxillary image is substantially zero.

14. The occlusal state identifying apparatus according to claim 8, wherein the processor is configured to output movement/rotation information indicating a movement amount and/or a rotation amount of the mandibular image and/or the maxillary image moved by executing the dynamic simulation.

15. A non-transitory computer-readable storage medium storing a program that causes a processor included in an occlusal state identifying apparatus to execute a process, the process comprising:

obtaining maxillary shape data and mandibular shape data;

arranging a maxillary image including a plurality of maxillary teeth corresponding to the obtained maxillary shape data and a mandibular image including a plurality of mandibular teeth corresponding to the obtained mandibular shape data such that a center of gravity of corresponding predetermined teeth match each other;

defining a state where maxillary teeth included in the maxillary image, which has fallen naturally, collide with mandibular teeth included in the mandibular image and stop, by executing a dynamic simulation based on the arranged maxillary image and the arranged mandibular image; and identifying a positional relationship between the maxillary image and the mandibular image obtained by the defined state as a positional relationship corresponding to an occlusal state of the maxillary teeth included in the maxillary image and the mandibular teeth included in the mandibular image.

* * * * *